US012565468B2

(12) United States Patent
Wei et al.

(10) Patent No.: US 12,565,468 B2
(45) Date of Patent: Mar. 3, 2026

(54) PROCESSES AND INTERMEDIATES FOR THE PREPARATIONS OF CARBOPROST AND CARBOPROST TROMETHAMINE, AND CARBOPROST TROMETHAMINE PREPARED THEREFROM

(71) Applicant: CHIROGATE INTERNATIONAL INC., Yangmei (TW)

(72) Inventors: Shih-Yi Wei, Yangmei (TW); Min-Kuan Hsu, Yangmei (TW); Jian-Bang Jheng, Yangmei (TW)

(73) Assignee: CHIROGATE INTERNATIONAL INC., Yangmei (TW)

( * ) Notice: Subject to any disclaimer, the term of this patent is extended or adjusted under 35 U.S.C. 154(b) by 0 days.

(21) Appl. No.: 17/408,864

(22) Filed: Aug. 23, 2021

(65) Prior Publication Data

US 2023/0097470 A1 Mar. 30, 2023

(51) Int. Cl.
*C07C 59/46* (2006.01)
*C07C 51/377* (2006.01)
*C07D 313/00* (2006.01)

(52) U.S. Cl.
CPC ............ *C07C 59/46* (2013.01); *C07C 51/377* (2013.01); *C07D 313/00* (2013.01); *C07B 2200/13* (2013.01)

(58) Field of Classification Search
CPC ...................................................... C07C 59/46
See application file for complete search history.

(56) References Cited

U.S. PATENT DOCUMENTS

| | | | | | |
|---|---|---|---|---|---|
| 3,728,382 | A | * | 4/1973 | Bundy | C07C 405/00 556/441 |
| 4,683,330 | A | * | 7/1987 | Aristoff | C07C 405/0083 564/453 |
| 4,775,692 | A | * | 10/1988 | Ohno | C07D 307/93 514/444 |
| 2013/0190404 | A1 | | 7/2013 | Li et al. | |
| 2018/0362457 | A1 | | 12/2018 | Buzder-Lantos et al. | |

FOREIGN PATENT DOCUMENTS

| | | | | | |
|---|---|---|---|---|---|
| CN | 1136938 | C | | 2/2004 | |
| CN | 102336693 | A | | 2/2012 | |
| CN | 102816099 | A | | 12/2012 | |
| CN | 111777537 | A | | 10/2020 | |
| EP | 2837621 | A1 | * | 2/2015 | A61K 31/165 |
| GB | 2495458 | B | * | 9/2016 | |
| OA | 2017/093770 | | | 6/2017 | |
| TW | 201733980 | A | | 10/2017 | |
| WO | 2008/081191 | A1 | | 7/2008 | |
| WO | 2012/010089 | A1 | | 1/2012 | |
| WO | WO-2015048736 | A1 | * | 4/2015 | A61K 31/557 |
| WO | WO-2017093770 | A1 | * | 6/2017 | A61K 31/5575 |

OTHER PUBLICATIONS

Shankar "Facile Route for Synthesis of (±)-Dinoprost, (±)-Carboprost and Its Analogs" Asian Journal of Chemistry; vol. 25, No. 2 (2013), 913-920.*
Iguchi "The synthesis of 15-methyl or 15,16-dimethyl prostaglandins" Prostaglandins Oct. 1973, vol. 4, Issue 4, pp. 535-538.*
Andersen "Omega chain methylated analogs of PGF2α and PGE2." Prostaglandins, 22(5), 809-30 1981.*
Snider "Separation of cis-trans isomers of prostaglandins with a cyclodextrin bonded column." Journal of Chromatography, 1986, 351(3), 548-53.*
Evans, D.A.; "A Stereochemical Model for Merged 1,2- and 1,3-Asymmetric Induction in Diastereoselective Mukaiyama Aldol Addition Reactions and Related Processes" Dart, M.J.; Duffy, J.L.; Yang, M.G. J .Am. Chem. Soc. 1996, 118, 4322.*
Ernest W. Yankee, et al.; Total Synthesis of 15-Methylprostaglandins; Journal of the American Chemical Society; 96(18); 5865-5876; Sep. 4, 1974.
Mats Hamberg, et al.; On the pH-dependent degradation of 15 (S )-15-methyl-prostaglandin $F_{2\alpha}$ (Carboprost); European Journal of Pharmaceutical Sciences; 3 (1995) 27-38.
CN 111777537 A dated Oct. 16, 2020 _ English Translation.
CN 102816099 A dated Dec. 12, 2012 _ English Translation.
CN 1136938 C dated Feb. 4, 2004 _ English Translation.
CN 102336693 A dated Feb. 1, 2012_ English Translation.
Office Action issued with a Search Report dated Jun. 7, 2022 from the Intellectual Property Office of Taiwan (IPO) for the corresponding Taiwan Patent Application No. 110131107.
Extended European Search Report issued for the corresponding EP Patent Application No. 22186007.5. dated Mar. 30, 2023.
Gordon L. Bundy, et al: "Synthesis and Biological Activity of Prostaglandin Lactones": Journal of Medicinal Chemistry: American Chemical Society: US, vol. 26, No. 8, Aug. 1983 (Aug. 1983), pp. 1089-1099, XP000999619.
Constantin Tanase et al: "Lactones in the Synthesis of Prostaglandins and Prostaglandin Analogs", International Journal of Molecular Sciences: vol. 22, No. 4, Feb. 4, 2021 (Apr. 4, 2021), p. 1572, XP055983291.
Mino R. Caira: "Crystalline Polymorphism of Organic Compounds", Topics in Current Chemistry; Springer Verlag Berlin Heidelberg; DE, vol. 198, Jan. 1998 (Jan. 1998), pp. 163-208, XP008166276.

* cited by examiner

*Primary Examiner* — David K O'Dell
(74) *Attorney, Agent, or Firm* — LADAS & PARRY LLP

(57) ABSTRACT

The invention relates to processes for preparing Carboprost or Carboprost Tromethamine, and intermediates prepared from the process, and 5,6-trans isomer free Carboprost or Carboprost Tromethamine prepared therefrom. The invention also relates to a novel crystalline form of Carboprost Tromethamine.

2 Claims, 6 Drawing Sheets

PROCESSES AND INTERMEDIATES FOR THE PREPARATIONS OF CARBOPROST AND CARBOPROST TROMETHAMINE, AND CARBOPROST TROMETHAMINE PREPARED THEREFROM

FIELD OF THE INVENTION

The present invention relates to novel processes and intermediates for the preparations of Carboprost and Carboprost Tromethamine, and a novel high melting point crystal of Carboprost Tromethamine prepared therefrom.

BACKGROUND OF THE INVENTION

Carboprost and Carboprost Tromethamine (INN, trade names Hemabate, Tham), as shown in the following Scheme A, are both synthetic prostaglandin analogues of $PGF_{2\alpha}$ (specifically, it is 15-methyl-$PGF_{2\alpha}$) with oxytocic properties. Carboprost and Carboprost Tromethamine can induce contractions and trigger abortion in early pregnanc, and can also reduce postpartum bleeding.

Scheme A

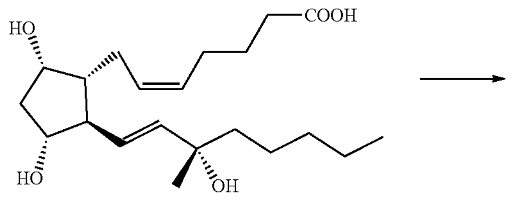

Carboprost

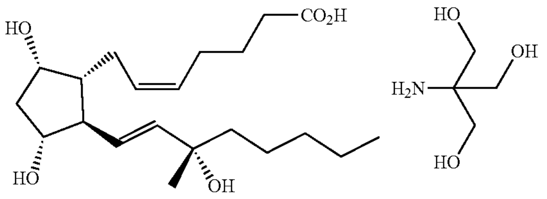

Carboprost Tromethamine

Although the current regulations restrict the content of impurities in active pharmaceutical ingredients (APIs) more and more stringently, almost all of the commercially available Carboprost and Carboprost Tromethamine still contain about 3% 5,6-trans isomers and about 2% 15(R)-epimers. The following Scheme B illustrates the chemical structures of Carboprost and isomers thereof, i.e., 5,6-trans Carboprost and 15-epi Carboprost. It appears that the methods for mass production of Carboprost or Carboprost Tromethamine in industry have some problems to be solved, especially in constructing the steric orientations of the cis-double bond at C5-C6 position and the tertiary alcohol at C15 position of Carboprost or Carboprost Tromethamine. It is also obvious that the current purification methods for removing the impurities of Carboprost or Carboprost Tromethamine are not effective and have to be improved.

Scheme B

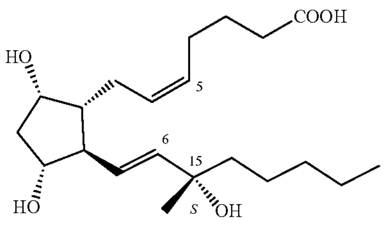

Carboprost

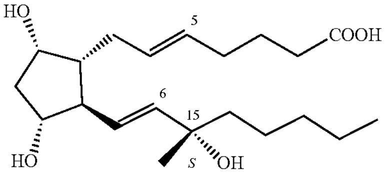

5,6-trans Carboprost

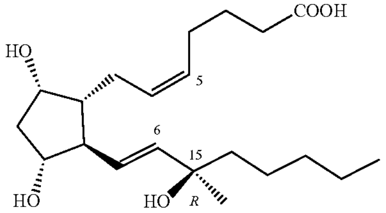

15-epi Carboprost

C15-(R/S)-Selectivity

Carboprost Tromethamine is the original product of Upjohn. The first scalable synthesis of Carboprost Tromethamine was described by chemists of Upjohn (Yankee et al., J. Am. Chem. Soc, 96(18), 5865-5876, 1974). As shown in the following Scheme C (1), the 15-methyl substituent was constructed from the benzoyl γ-lactone-enone of Formula a with trimethylaluminum or with methylmagnesium bromide. However, the selectivity of the 15(S)-product was only 50% in both cases, which means that the process has no selectivity. WO 2008/081191 discloses that the alkylation of triethylsily γ-lactone-enone of Formula b and methylmagnesium chloride can obtain 15(S)-product with a highest selectivity of 70%, as shown in the following Scheme C (2). WO 2017/093770 discloses that the alkylation of p-phenylbenzoyl γ-lactone-enone of Formula c and methylmagnesium bromide can obtain 15(S)-product with a selectivity of only 55%, and it also discloses the use of various chiral additives in order to increase the selectivity of the 15(S)-product, and found that the addition of (S)-Taddol can increase the selectivity to 70%, as shown in the following Scheme C (3). However, the highest selectivity disclosed in WO 2017/093770 is at most the same as that disclosed in WO 2008/081191.

Scheme C (1)

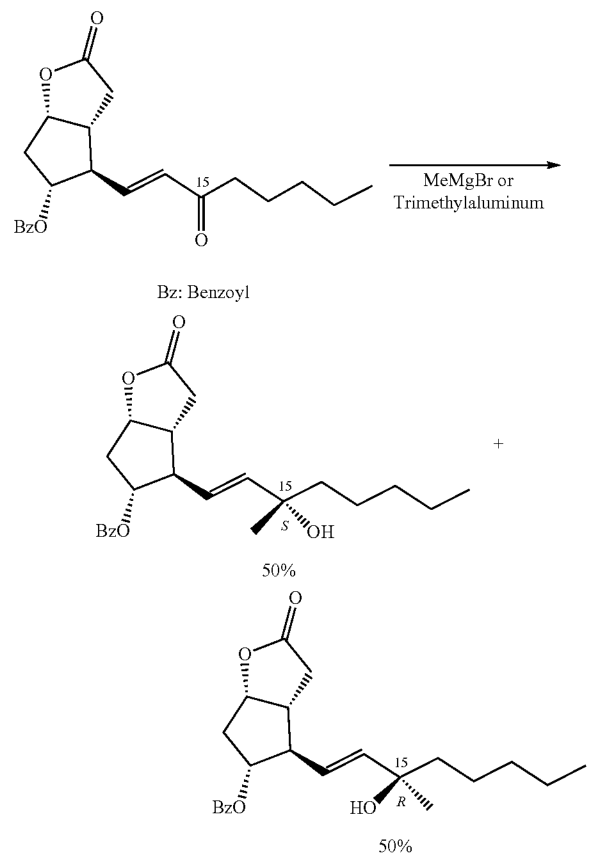

(2)

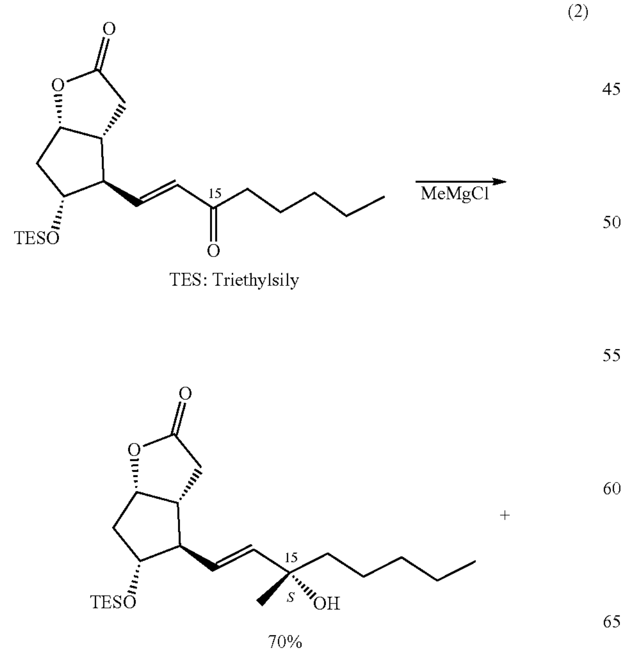

-continued

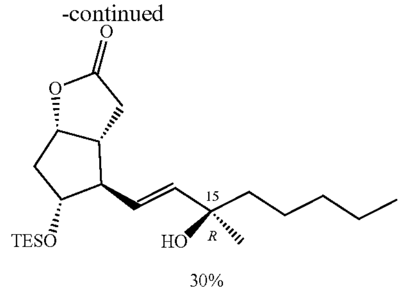

(3)

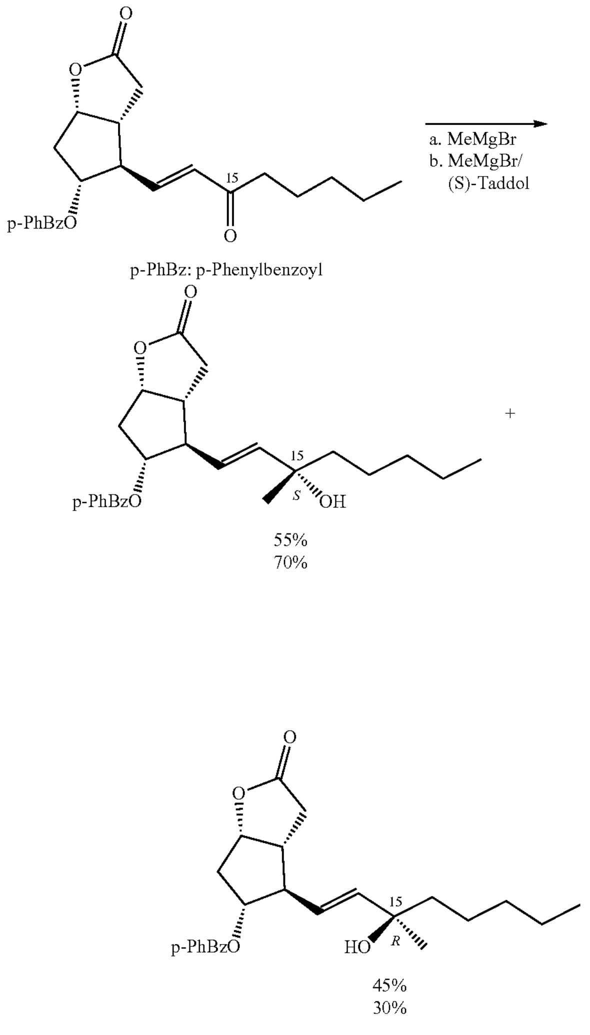

C5,6-(Trans/Cis)-Selectivity

WO 2008/081191 discloses that carrying out the Wittig reaction at ambient temperature and in the solvent of dimethyl sulfoxide (DMSO) as disclosed by Yankee et al., will generate 6 to 8% undesired 5,6 trans-isomer, as shown in the following Scheme D (1). WO 2008/0181191 further discloses that the reaction at a lower temperature, i.e., from −5° C. to +5° C., can reduce the content of the 5,6 trans-isomer to about 3%, as shown in the following Scheme D (2). Given the above, since the commercially available Carboprost and Carboprost Tromethamine all contain about 3% 5,6-trans isomer, it seems that changing the reaction conditions of the Wittig reaction may be useless in further reducing the content of 5,6-trans isomer generated therefrom.

Scheme D (1)

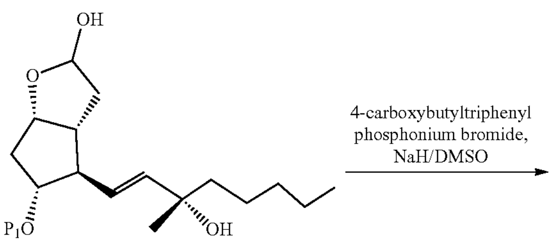

$P_1$: H, Benzoyl or Trimethylsilyl

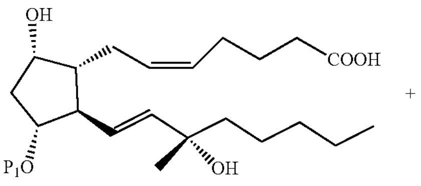

6,6-cis
~92%

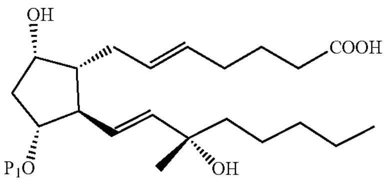

5,6-trans
~8%

-continued

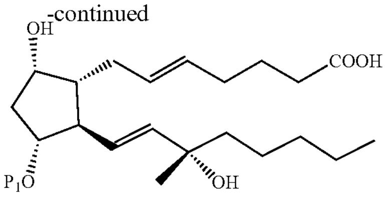

5,6-trans
~3%

5,6-trans
~8%

(2)

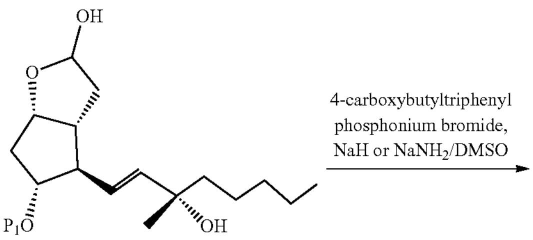

$P_1$: Triethylsilyl

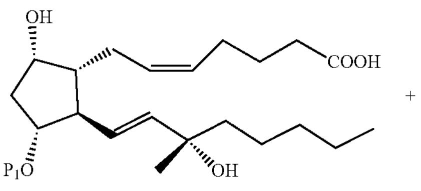

5,6-cis
~97%

Removing 15(R)-Epimer and Trans Isomer by Purification of Carboprost Methyl Ester As disclosed by Yankee et al. and in Eur, J, Pharm, Sci, 3, 27-38 (1995), the allylic tertiary alcohol at C15 position of Carboprost is very unstable; thus, just a few acids or a little heat will result in producing a large amount of 15(R)-epimer rapidly via epimerization. Due to this reason, the current methods of mass production of Carboprost or Carboprost Tromethamine in industry do not construct the stereochemistry of allylic tertiary alcohol in the intermediates formed in early steps, since the stereochemistry of the allylic tertiary alcohol is difficult to be maintained until the final stage. Therefore, almost all of the current methods of mass production of Carboprost or Carboprost Tromethamine in industry construct the stereochemistry of the allylic tertiary alcohol until forming the structure of the final product or in the intermediates formed in late steps, or remove the undesired 15(R)-epimer and trans isomer after forming the final product.

Although the final product Carboprost Tronethamine is a crystalline solid at room temperature, it is still very difficult to efficiently remove the 15(R)-epimer and trans isomer simultaneously only by crystallization purification. In addition, since the polarity of Carboprost is very large, it is more difficult to remove the 15(R)-epimer and trans isomer from Carboprost by chromatography.

Consequently, the isomers generated during the formation of Carboprost or Carboprost Tromethamine cannot be effectively removed, and there is no any suitable late-step intermediate used for separating and removing isomers in the prior art methods. In order to purify the final products, two additional steps are required to create a late-step intermediate that is suitable for use in separation and removal of isomers. As disclosed in the prior art references, e.g., J, Am. Chem. Soc., 96(18), 5865-5876, 1974; WO 2008/081191; WO 2017/093770; CN 111777537; and CN 102816099, Carboprost has to be esterified to form Carboprost methyl ester, then the 15(R)-epimer and trans isomer of Carboprost methyl ester are removed by chromatography, and the Carboprost methyl ester is hydrolyzed into Carboprost with higher purity, but the yield and purity in such method are very unsatisfactory. CN 1136938 C discloses the use of expensive and special simulated moving bed (SMB) chromatography to separate and remove the isomers of Carboprost methyl ester, but the purity of the final product is still not good enough. CN 102816099 discloses the use of analytical-grade HPLC column chromatography packing (5 μm) for separation, but the trans isomers still cannot be removed completely. In addition, since the amount that can be separated by the method of CN 102816099 is small, such method is difficult to be used for industrial-grade mass production.

SUMMARY OF THE INVENTION

Given the above, there is a need to discover and develop a method for preparing high purity Carboprost or Carboprost Tromethamine, which can significantly reduce the formation of impurities or isomers including 15(R)-epimer and trans isomer, and can also effectively remove the generated impurities or isomers.

The objective of the present invention is to provide an efficient process for producing Carboprost or Carboprost Tromethamine. The process includes a macrolactonization step, which can effectively remove 5,6-trans isomer. The process also includes a methylation step of mecrolactone-enone for constructing the orientation of tertiary alcohol at C15 position of Carboprost. The 15(5)-selectivity of methylation of macrolactone-enone is much higher than that of methylation of γ-lactone-enone in all previous examples. The present invention also provides a novel purification process that can effectively remove all isomers and can produce Carboprost and Carboprost Tromethamine more efficiently, thereby forming final products with high purity, high melting point, and good stability.

In one aspect, the present invention provides a process for preparing high purity Carboprost or Carboprost Tromethamine containing no more than about 1% total isomers from a compound of Formula 1a containing about 1 to 10% 5,6-trans isomer:

Ia

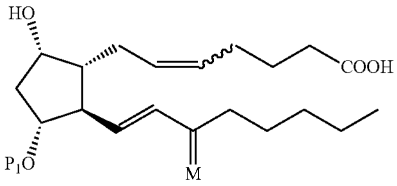

wherein

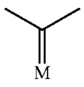

is

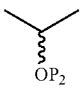 , 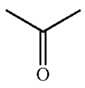 , or a protecting group for carbonyl groups; and $P_1$ and $P_2$ are H or protecting groups for hydroxy groups.

In another aspect, the present invention provides a process for preparing high purity Carboprost or Carboprost Tromethamine containing no more than about 1% total isomers from a compound of Formula 1b containing about 1 to 10% 5,6-trans isomer.

Ib

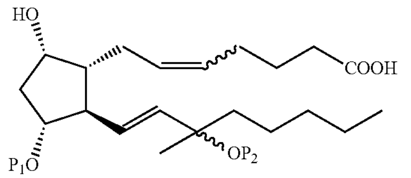

wherein $P_1$ and $P_2$ are H or protecting groups for hydroxy groups.

In another aspect, the present invention provides a process for purification of Carboprost, which is effective to purify low purity Carboprost containing a large amount of isomers, such as about 1 to 10% 5,6-trans isomer and about 1 to 50% 15(R)-epimer, to a high purity Carboprost containing no more than about 1% total isomers.

In one another aspect, the present invention provides a macrolactone-enone intermediate of Formula 2a', which is a novel intermediate for preparing Carboprost or Carboprost Tromethamine, 2a'

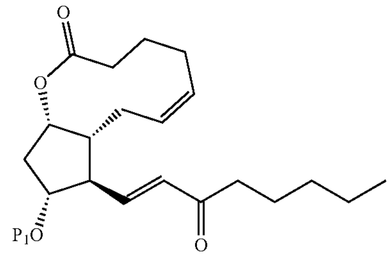

wherein $P_1$ is H or a protecting group for hydroxy groups.

In another aspect, the present invention provides a process for preparing a macrolactone-tertiary alcohol of Formula 3, which is an intermediate for preparing Carboprost or Carboprost Tromethamine,

3

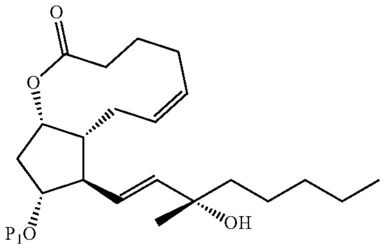

wherein $P_1$ is H or a protecting group for hydroxy groups, from a macrolactone-enone of Formula 2a' with a methylation reagent.

In one another aspect, the present invention provides a high melting point (106.4±1° C.) crystal of Carboprost Tromethamine having an X-ray powder diffraction (XRPD) pattern exhibiting characteristic peaks at the following 20 reflection angles: 6.9±0.2°, 10.3±0.2°, 18.8±0.2°, and 21.9±0.2°.

In yet another aspect, the present invention provides a process for preparing a high melting point crystal of Carboprost Tromethamine, comprising the use of a solvent of anhydrous acetonitrile.

DETAILED DESCRIPTION OF THE INVENTION

Definition

Figure 1:
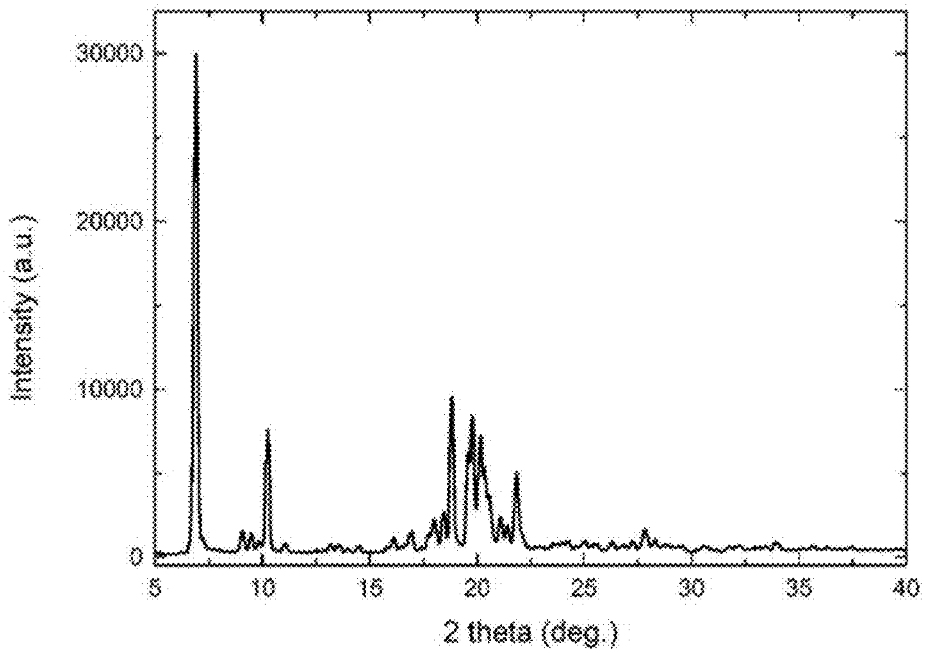
FIG. 1 shows the X-ray powder diffraction (XRPD) pattern of the Carboprost Tromethamine crystal of the present invention.

The use of the word "a" or "an" when used in conjunction with the term "comprising" in the claims and/or the specification may mean "one," but is also consistent with the meaning of "one or more," "at least one," and "one or more than one." The use of the term "or" in the claims is used to mean "and/or" unless explicitly indicated to refer to alternatives only or unless the alternatives are mutually exclusive, although the disclosure supports a definition that refers only to alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In the depiction of the compounds given throughout this description, a wedged bold bond ( ) means a bond projecting above the plane of the paper; a wedged hashed bond ( ) means a bond projecting below the plane of the paper; and a wavy bond ( ) means a bond projecting almost half above and half below the plane of the paper.

When used herein, the term "high purity Carboprost or Carboprost Tromethamine," "high purity Carboprost" or "high purity Carboprost Tromethamine" means that Carboprost and/or Carboprost Tromethamine in question contains no more than about 1% total isomers, preferably no more than about 0.8% total isomers or no more than about 0.5% total isomers, and more preferably no more than about 0.3% total isomers. The isomers or impurities indicated herein include 5,6-trans isomers, 15(R)-epimers, and any other stereoisomers.

When used herein, the term regarding substantially free of 5,6-trans isomer or the like means that a compound in question does not contain more than about 0.5%, about 0.3%, about 0.2%, about 0.1%, about 0.05%, or about 0.03% of impurities or isomers, such as 5,6-trans isomer, or contains a none-detectable level of impurities or isomers, such as 5,6-trans isomer measured by HPLC, for which the detection limit is not more than about 0.03%.

Unless otherwise specified, the term "protecting group for hydroxy groups" has the meaning conventionally defined in organic synthetic chemistry, i.e., a group capable of protecting a hydroxyl group or moiety of a compound against the attacks of a chemical reaction. Examples of the hydroxyl protecting group include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl, acetyl, substituted acetyl, benzoyl, substituted benzyl, and $SiR_aR_bR_c$ wherein $R_a$, $R_b$ and $R_c$ are each independently unsubstituted or substituted alkyl or unsubstituted or substituted aryl, such as $C_{1-4}$ alkyl, phenyl, benzyl, substituted phenyl, and substituted benzyl.

Unless otherwise specified, the term "protecting group for carbonyl groups" has the meaning conventionally defined in organic synthetic chemistry, i.e., a group capable of protecting a carbonyl group or moiety of a compound against the attacks of a chemical reaction. Examples of the carbonyl protecting group include, but are not limited to, dialkyl ketal, diaralkyl ketal, diacetyl ketal, dithio ketal, 1,3-dioxane, 1,3-dioxolane, 1,3-dithiane, 1,3-dithiolane, and 1,3-oxathiolane. Preferred protecting groups for carbonyl groups include dialkyl ketal, 1,3-dioxane, and 1,3-dioxolane.

Each of the above mentioned groups such as alkyl and aryl may optionally be substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl, or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl, pyrrolidinonyl, and the like. Unless otherwise specified, the term "alkyl" used herein refers to a straight or branched hydrocarbon group containing 1 to 8, 1 to 6, or 1 to 4 carbon atoms, such as methyl, ethyl, isopropyl, tert-butyl, and the like; or a cyclic saturated hydrocarbon group having 3 to 10 or 3 to 8 carbon atoms, such as cyclopropyl, cyclopentyl, cyclohexyl, and the like. The term "aryl" used herein refers to a monocyclic or polycyclic aromatic hydrocarbon radical, and having 6 to 20, 6 to 18, or 6 to 12 carbon atoms, such as phenyl, naphthyl, anthryl, phenanthryl and the like.

Synthesis of High Purity Carboprost from Known Prostaglandin Intermediates of Formula 1a or Formula 1b According to the present invention, the high purity Carboprost or Carboprost Tromethamine can be prepared according to the reactions shown in Scheme 1 and Scheme 2:

Scheme 1

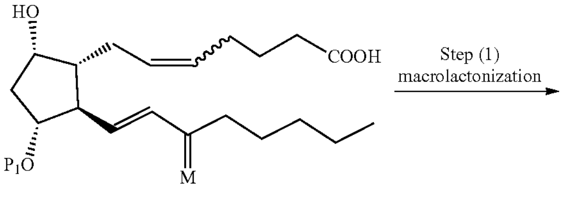

1a

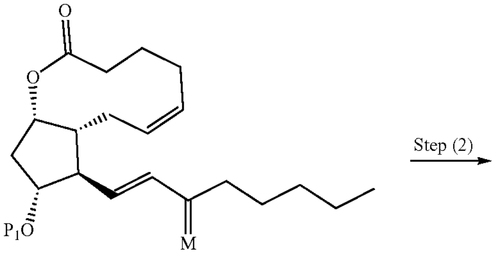

2a

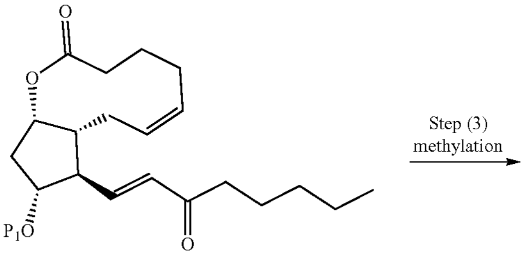

2a'

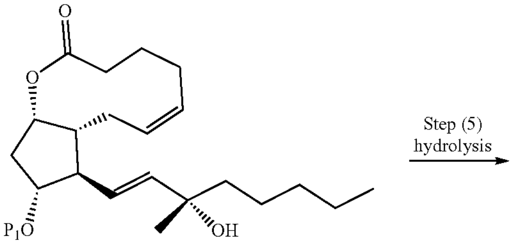

3

Step (4)
chromatography
separation

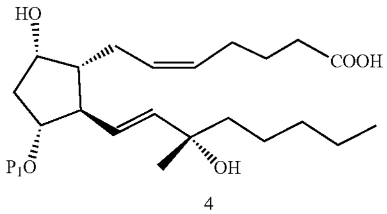

4

Scheme 2

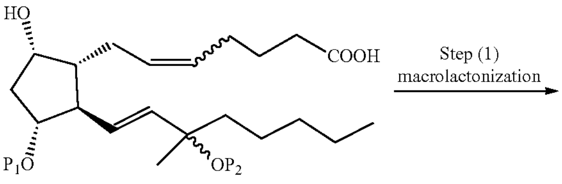

1b

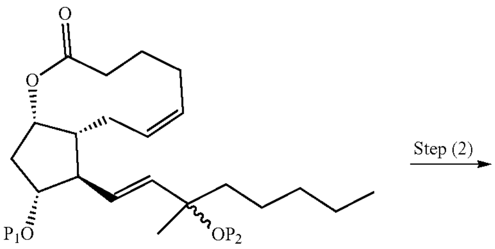

2b

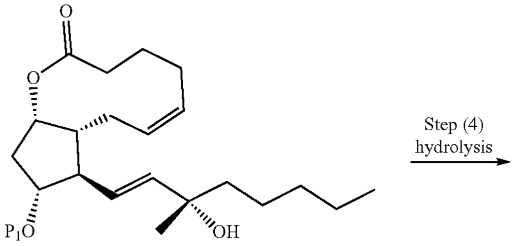

3

Step (3)
chromatography
separation

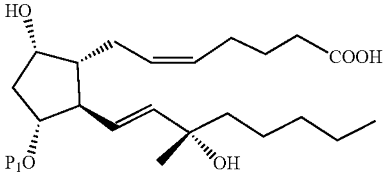

4

The compound of Formula 1a in Scheme 1, wherein

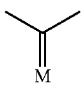

is

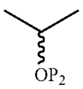
,
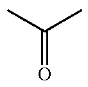

or a protecting group for carbonyl groups; and $P_1$ and $P_2$ are protecting groups for hydroxy groups, is a well-known prostaglandin $F_{2\alpha}$ intermediate. The compound of Formula 1b in Scheme 2, wherein $P_1$ and $P_2$ are protecting groups for hydroxy groups, is also a well-known 15-methyl prostaglandin $F_{2\alpha}$ intermediates. The two prostaglandin intermediates can be prepared from a famous intermediate, Corey lactone, via a Wittig reaction. Due to different reaction conditions of the Wittig reaction, the two prostaglandin intermediates almost all contain about 1% to about 10% 5,6-trans isomer.

As shown in Step (1) of Scheme 1 and Step (1) of Scheme 2, the macrolactonization reaction may involve the activation of the carboxyl or/and hydroxyl functional groups. In this route, the macrolactonization reaction comprises the initial formation of a thioester with a suitable reagent, which includes, but is not limited to, S-pyridin-2-yl chloromethanethioate, 2,2'-dipyridyl disulfide/triphenylphosphine, or 4-tert-butyl-2-(2-(4-tert-butyl-1-isopropyl-1H-imidazol-2-yl)disulfanyl)-1-isopropyl-1H-imidazole/triphenylphosphine.

The macrolactonization reaction may alternatively involve the initial formation of a mixed anhydride with a suitable reagent in the presence or absence of a base or a Lewis acid. Suitable reagents for forming the mixed anhydrides include, but are not limited to, 2,4,6-trichlorobenzoyl chloride, 2-nitro-6-nitrobenzoic anhydride, p-nitrofluoromethylbenzoic anhydride, p-nitrobenzoic anhydride, and the like. Examples of the suitable bases include 4-(dimethylamino)pyridine, pyrolidinopyridine, triethylamine, N,N-diisopropylethylamine, and isopropyldiethylamine. Examples of suitable Lewis acids include $Sc(OTf)_3$, $TiCl_4$, $AgClO_4$, trimethylsilyl chloride (TMSCl) and $TiCl_2(OTf)$.

The macrolactonization reaction can also be achieved by using a condensation reagent and a base in an appropriate solvent. Suitable condensation reagents include, but are not limited to, N,N'-dicyclohexylcarbodiimide, 2-chloro-1-methyl-pyridium iodide, 2-chloro-4,5-dihydro-1,3-dimethyl-1H-imidazolium chloride, N,N-diphenylchlorophenylmethyleniminium chloride, cyanuric chloride, 1,3-dimethyl-2-chloroimidazolium chloride, N,N,N,N-tetramethylchloroformamidinium chloride, and the like. Examples of suitable bases include pyridine, triethylamine, diisopropylethylamine, 4-dimethylaminopyridine (DMAP), and the like. Suitable solvents for the condensation reaction include methylene chloride, tetrahydrofuran, and 1,2-dichloroethane, and a mixture thereof.

Upon analyzing a resultant compound of Formula 2a, 2a', 2b, 3 or 4 by HPLC or UPLC, it is unexpectedly found that the resultant compound of Formula 2a, 2a', 2b, 3 or 4, contains no more than about 0.1% of the 5,6-trans isomer or less, which reveals that the macrolactonization reaction exhibits a high cis-selectivity; that is, the 5,6-cis compounds of Formula 1a or 1b dominate in the macrolactonization reaction whereas the 5,6-trans compounds of Formula 1a or 1b hardly undergo the macrolactonization reaction.

Step (2) of Scheme 1 involves a deprotection and an oxidation of the compound of Formula 2a, wherein

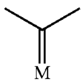

is

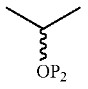

, by removing the $P_2$ at the ω-side chain and/or the $P_1$. The conditions for carrying out the deprotection reactions are obvious to persons skilled in the art. For example, the macrolactone of Formula 2a wherein $P_1$ and $P_2$ are tetrahydropyranyl protecting groups is dissolved in a suitable solvent, such as methanol or a solvent mixture of acetone and water in a volumetric ratio of 5 to 1; treated with a deprotecting agent such as hydrogen chloride, p-toluenesulfonic acid, or pyridium p-toluenesulfonate; and stirred at room temperature for 10 minutes to 10 hours. The reaction is quenched with a base, e.g., ammonium hydroxide or the like, and subjected to a work-up procedure conducted in a conventional manner. The deprotected product of Formula 2a, wherein $P_1$ and $P_2$ are H, is oxidated with a suitable oxidant such as $MnO_2$ or 2,3-dichloro-5,6-dicyanobenzoquinone (DDQ), to form the macrolactone-enone of Formula 2a', wherein $P_1$ is H.

For example, the macrolactone of Formula 2a wherein $P_1$ is a tetrahydropyranyl protecting group and $P_2$ is a tert-butyldimethylsilyl protecting group is dissolved in a suitable solvent, such as tetrahydrofuran (THF); treated with a deprotecting agent such as tetrabutylammonium fluoride (TBAF); and stirred at room temperature for 10 minutes to 10 hours. The reaction is subjected to a work-up procedure conducted in a conventional manner. The deprotected product of Formula 2a, wherein $P_1$ is a tetrahydropyranyl protecting group and $P_2$ is H, is then oxidated with a suitable oxidant such as Collins oxidant, Swern oxidant, PCC oxidant, PDC oxidant, and TEMPO oxidant, preferably TEMPO oxidation, to form the macrolactone-enone of Formula 2a', wherein $P_1$ is a tetrahydropyranyl protecting group.

Step (2) of Scheme 1 also involves a deprotection of the compound of Formula 2a, wherein

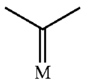

is a protecting group for carbonyl groups. The conditions for carrying out the deprotection reactions are obvious to persons skilled in the art. For example, the macrolactone of Formula 2a wherein

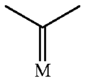

is a 1,3-dioxane protecting group and $P_1$ is H, is dissolved in a suitable solvent, such as THF or acetone; treated with a deprotecting agent such as 1M HCl solution; and stirred at room temperature for 10 minutes to 10 hours. The reaction is quenched with a base, e.g., saturated $NaHCO_3$ solution or the like, and subjected to a work-up procedure conducted in a conventional manner, to form the macrolactone-enone of Formula 2a', wherein $P_1$ is H.

Moreover, Step (2) of Scheme 2 involves a deprotection of the compound of Formula 2b, wherein $P_2$ is a protecting group for hydroxy groups, by removing the $P_2$ at the ω-side chain and/or the $P_1$. The conditions for carrying out the deprotection reactions are obvious to persons skilled in the art.

Step (3) of Scheme 1 shows a methylation of the macrolactone-enone of Formula 2a' wherein $P_1$ is a protecting group for hydroxy groups, to form a macrolactone-tertiary alcohol of Formula 3a. According to the present invention, the methylation agent includes, but is not limited to, MeLi, MeMgCl, MeMgBr, MeMgI, $Me_3Al$, or a mixture thereof. Preferably, the methylation agent is MeMgCl, MeMgBr, MeMgI, MeLi, or a mixture thereof. Most preferably, the methylation agent is MeLi. The non-limiting, suitable solvent used in the reaction can be selected from tetrahydrofuran, ether, toluene, hexane, or a mixture thereof. The reaction is carried out at a temperature ranging from about −120° C. to the room temperature, preferably from about −100° C. to about −40° C. The methylation agent is used in an amount such that the reactants are completely reacted as monitored by thin layer chromatography (TLC).

It is unexpectedly found that the reaction of the macrolactone-enone and a methyl Grignard reagent as the methylation agent exhibits up to about 65% 15(S)-selectivity. However, as shown in Scheme A (1), the 15(S)-selectivity of the reaction of γ-lactone-enone and a methyl Grignard reagent is only 50%. It appears that the structure of macrolactone is beneficial to the 15(S)-selectivity than γ-lactone. In addition, the present invention surprisingly shows that the use of a low cost and more convenient MeLi as the methylation agent, the methylation of the macrolactone-enone can have a 15(5)-selectivity of about 75% or more, which is very high and cannot be achieved even using a chiral additive in the reaction of γ-lactone (WO 2017/093770, using (S)-Taddol, the highest selectivity is merely 70%).

Step (4) of Scheme 1 and Step (3) of Scheme 2 involve a purification of the macrolactone-tertiary alcohol of Formula 3, for removing 15(R)-epimer. Typically, the separation of isomers of Carboprost is the most expensive and time-consuming step in the mass production of carboprost. However, the cost for separation of isomers of the present invention is much lower than the prior art techniques, e.g., J, Am. Chem. Soc., 96(18), 5865-5876, 1974; WO 2008/081191; WO 2017/093770; CN 111777537; and CN 102816099A. The reasons are listed as follows:

(a) In the prior art techniques, Carboprost has to be esterified to form an intermediate, Carboprost methyl ester, which is suitable for use in removing isomers, and then the isomers of Carboprost methyl ester can be removed by chromatographic purification. However, it is unexpectedly found that late-step intermediate of Formula 3 is an intermediate that is suitable for use in removing isomer; thus, an additional esterification reaction is unnecessary to be used in the present invention.

(b) When using chromatographic purification to remove 5,6-trans isomer and 15(R)-epimer of Carboprost intermediates, 5,6-trans isomer (HPLC, RRT 0.93) is usually more difficult to be separated than 15(R)-epimer (HPLC. RRT 0.88). CN 102816099 even uses an analytical-grade HPLC with filler (5 μm) in order to remove 5,6-trans isomer (RRT 0.93) of Carboprost methyl ester. In contrast, the intermediate of Formula 3, as well as the compound of Formula 2a', formed after macrolactonization have substantially free of 5,6-trans isomer, thus, a general silica gel column chromatography for industrial mass production can be simply used to separate 15(R)-epimer that is easier to be removed.

(c) The methylation of macrolactone-enone of the present invention exhibits higher selectivity, so the amount of the generated 15(R)-epimer is fewer and can be removed more easily.

In Step (4) of Scheme 1 and Step (3) of Scheme 2, the chromatographic purification can be performed using ester-type, ether-type, ketone-type or halogenated solvents, or the like or a mixture thereof. For using a mixture of dichloromethane and acetone, good separation can also be achieved with ethyl acetate, isopropyl acetate, methyl tert-butyl ether, acetone, methyl ethyl ketone, or a mixture thereof. By chromatography, the amount of the undesired 15(R)-epimer can be decreased to a specified limit, i.e., ≤ about 0.5%, ≤ about 0.3%, ≤ about 0.2%, ≤ about 0.1%, or less.

As shown in Step (5) of Scheme 1 and Step (4) of Scheme 2, the macrolactone-tertiary alcohol of Formula 3 is hydrolyzed to Carboprost in methanol solution by treatment with lithium hydroxide solution. Acidification to obtain Carboprost has to be performed quickly, to avoid epimerization in the acid medium.

Accordingly, the present invention provides a process for preparing Carboprost containing no more than 1% total isomers, the process comprising the steps of:

(1) macrolactonization of a compound of Formula 1a containing 1 to 10% 5,6-trans isomer 1a

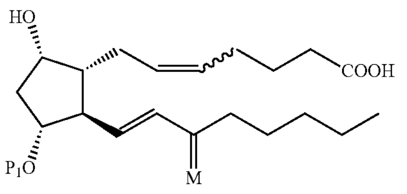

wherein

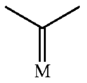

is

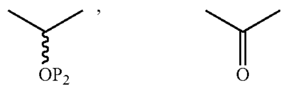

or a protecting group for carbonyl groups; and $P_1$ and $P_2$ are H or protecting groups for hydroxy groups, to form a compound of Formula 2a:

2a

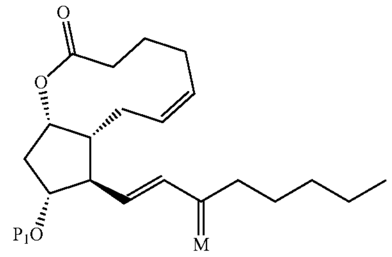

wherein

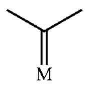

, $P_1$ and $P_2$ are as defined above for Formula 1a;

(2) removing the protecting group for carbonyl groups of the compound of Formula 2a, wherein

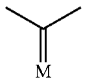

is a protecting group for carbonyl group; or removing $P_2$ and/or oxidizing the compound of Formula 2a, wherein

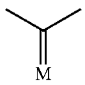

is

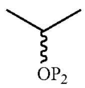

;

to form a compound of Formula 2a':

2a'

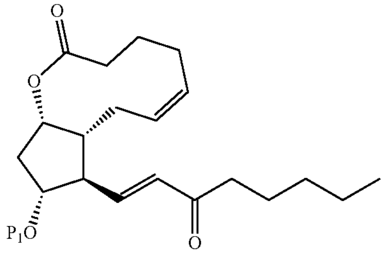

wherein $P_1$ is H or a protecting group for hydroxy groups;

(3) methylation of the compound of Formula 2a' with a methylation reagent, to form a compound of Formula 3:

3

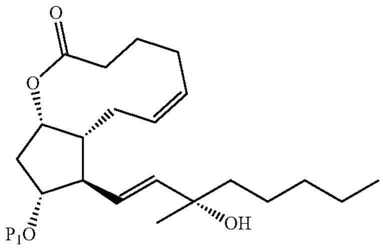

wherein $P_1$ is H or a protecting group for hydroxy groups;

(4) chromatographic separation of the compound of Formula 3 to remove isomers;

(5) hydrolysis of the compound of Formula 3, to form a compound of Formula 4:

4

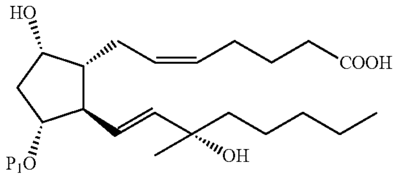

wherein $P_1$ is H or a protecting group for hydroxy groups; and optionally performing a deprotecting reaction of the compound of Formula 2a, 2a', 3, or 4, when $P_1$ is a protecting group for hydroxy groups, to form a compound of Formula 2a, 2a', 3, or 4, wherein $P_1$ is H.

The present invention also provides a process for preparing high purity Carboprost containing no more than 1% total isomers, the process comprising the steps of:

(1) macrolactonization of a compound of Formula 1b containing 1 to 10% 5,6-trans isomer and 1 to 50% 15(R)-epimer, 1b

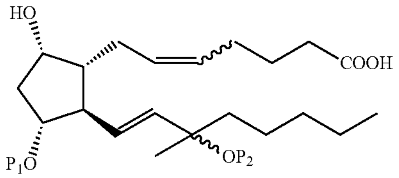

wherein $P_1$ and $P_2$ are H or protecting groups for hydroxy groups, to form a compound of Formula 3a:

3a

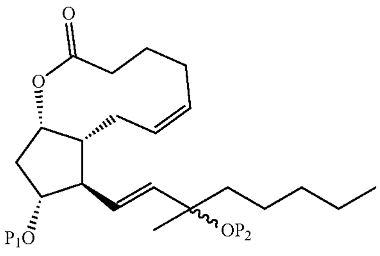

wherein $P_1$ and $P_2$ are as defined above;

(2) performing a deprotection reaction of the compound of Formula 3a, when $P_1$ is H or a protecting group for hydroxy groups, and $P_2$ is a protecting group for hydroxy groups, to form a compound of Formula 3a, wherein $P_1$ is H or a protecting group for hydroxy groups, and $P_2$ is H;

(3) chromatographic separation of the compound of Formula 3a, wherein $P_1$ is H or a protecting group for hydroxy groups, and $P_2$ is H, to remove isomers;

(4) hydrolysis of the compound of Formula 3a, to form a compound of Formula 4:

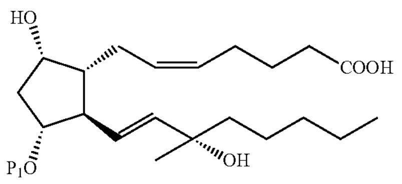

4 wherein $P_1$ is H or a protecting group for hydroxy groups; and (5) optionally preforming a deprotecting reaction of the compound of Formula 3a or 4, when $P_1$ is a protecting group for hydroxy groups, to form a compound of Formula 3a or 4, wherein $P_1$ is H.

Purification of a Low Purity Carboprost which Contains an Excess Amount of Isomers Crude Carboprost obtained from conventional reactions or due to an overreaction of epimerization normally contains a large amount or an excess amount of isomers. The inventors found that Carboprost containing an excess amount of isomers can be further purified by using the process of the present invention. The process of the present invention comprises providing a low purity Carboprost containing at least about 1 to 10% 5,6-trans isomer and about 1 to 50% 15(R)-epimer; macrolactonization of the low purity Carboprost to form a macrolactone-tertiary alcohol; chromatographic separation of excess isomers of the macrolactone-tertiary alcohol; and hydrolysis of the macrolactone-tertiary alcohol, to form a high purity Carboprost containing no more than about 1% total isomers.

Accordingly, the present invention provides a process for purification of Carboprost, comprising the steps of:

(1) macrolactonization of a low purity Carboprost containing 1 to 10% 5,6-trans isomer and 1 to 50% 15(R)-epimer, to form a compound of Formula 3b:

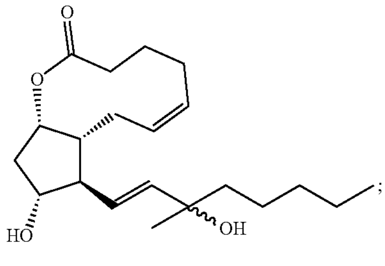

;

3b (2) chromatographic separation of isomers of the compound of Formula 3b; and (3) hydrolysis of the compound of Formula 3b, to form a high purity Carboprost containing no more than 1% total isomers.

Carboprost Salt Formation with Tromethamine

To form Carboprost Tromethamine from Carboprost, the process further comprises a salt formation with tromethamine, and crystallization of Carboprost Tromethamine. The salt formation and crystallization steps may follow the method disclosed in CN 102336693 or WO 2017/093770. In general, Carboprost can be first dissolved in a suitable solvent, such as acetone, acetonitrile, methanol, ethanol, isopropyl alcohol, and a combination thereof; then tromethamine in a suitable solvent, such as water, methanol, ethanol, isopropanol, and a combination thereof, can be added to the solution; and the mixture can be heated to about 85° C. for about 1 hours to form a homogeneous solution. Thereafter, the homogenous solution can be allowed to cool down to about 60° C., and a white solid slowly starts to precipitate. The reaction mixture can be further cooled down to room temperature, and then filtered to obtain the white crystal of Carboprost Tromethamine. The melting point of the white crystal thus obtained is typically about 95° C. to 105° C. as originally disclosed by Pfizer (e.g., the prescribing information of Hemabate® provided by Pfizer).

In case of Example 1 of CN 102336693, about 1.20 g Carboprost Tromethamine was precipitated during lowering the temperature from the mixture of 100 ml acetonitrile and 0.5 ml water, and the melting point of the white crystal is measured as 103.97° C. (see FIG. 2). The present inventors repeated Example 1 of CN 102336693 and found that the melting point of the obtained Carboprost Tromethamine crystal is measured as 103.41° C.

In case of Example 1g of WO 2017/093770, about 593 g Carboprost Tromethamine was precipitated from the mixture of isopropanol and acetone. WO 2017/093770 does not disclose the melting point of the Carboprost Tromethamine crystal obtained from Example 1g. The present inventors repeated Example 1g of WO 2017/093770 and found that the melting point of the obtained Carboprost Tromethamine crystal is measured as 97.49° C.

The melting points of the above mentioned known Carboprost Tromethamine crystals range from about 97° C. to about 104° C., which are indeed within the scope as originally provided by Pfizer (95° C. to 105° C.).

Recrystallization of Carboprost Tromethamine

The recrystallization on Carboprost Tromethamine may provide effects on decreasing the content of 15(R)-isomer. The recrystallization methods of Carboprost Tromethamine have been disclosed in CN 102336693 and WO 2017/093770. The present inventors repeated the method CN 102336693 disclosed using water with acetone, and found that the recrystallized Carboprost Tromethamine has a melting point of 103.85° C. as measured. The present inventors also repeated the method WO 2017/093770 disclosed using isopropanol with acetone, and found that the recrystallized Carboprost Tromethamine has a melting point of 99.46° C. as measured.

It is an unexpectedly found that a specially high melting point Carboprost Tromethamine crystal can be obtained by a recrystallization process of Carboprost Tromethamine using a specific solvent of anhydrous acetonitrile. The high melting point Carboprost Tromethamine crystal thus formed has a differential scanning calorimetry (DSC) thermogram pattern comprising an endothermic peak with a peak maximum of 106.4±1.0° C., which is obviously higher than the upper limit of the melting point range originally provided by Pfizer and that of the above mentioned Carboprost Tromethamine crystals disclosed in the prior art.

Preparation of the High Melting Point Carboprost Tromethamine Crystal

The present invention provides a process for preparing a high melting point crystalline form of Carboprost Tromethamine, comprising the steps of:

a. adding Carboprost Tromethamine into anhydraous acetonitrile to form a mixture, wherein the anhydrous acetonitrile is in an amount of from about 80 to 250 ml per 1 g of Carboprost Tromethamine;

b. heating the mixture to a temperature ranging from about 70° C. to 90° C. to give a homogeneous solution;

c. cooling down the homogeneous solution to form the crystalline form of Carboprost Tromethamine; and d. optionally isolating the crystallized product.

In some embodiments, the mixture can be heated to about 80° C. for completely dissolving Carboprost Tromethamine; then the homogenous solution can be slowly cooled down, and a white solid is slowly started to precipitate; and the mixture can be further cooled down to room temperature, and then filtered and dried to obtain the crystalline form of Carboprost Tromethamine.

In some embodiments, the amount of the anhydrous acetonitrile used in step a ranges from about 80 to 250 ml, about 100 to 220 ml, or about 150 to 200 ml, per 1 g of Carboprost Tromethamine; the anhydrous acetonitrile has a water content of less than about 0.05%, less than about 0.01%, less than about 0.005%, or less than about 0.001% (w/w); and the process is preferably carried out without adding water. The crystalline form of Carboprost Tromethamine prepared from the process has a differential scanning calorimetry (DSC) thermogram pattern comprising an endothermic peak with a peak maximum of 106.4±1.0° C., which is higher than the other known crystalline forms of Carboprost Tromethamine. Since the Carboprost Tromethamine crystal obtained by the present invention has the highest melting point compared to all other known Carboprost Tromethamine crystals, it is the most stable crystalline form of Carboprost Tromethamine.

Moreover, the high melting point Carboprost Tromethamine crystal of the present invention has an X-ray powder diffraction (XRPD) pattern exhibiting characteristic peaks at the following 20 reflection angles: 6.9±0.2°, 10.3±0.2°, 18.8±0.2°, and 21.9±0.2°, which is obviously different from the 20 reflection angles: 6.6±0.2°, 9.9±0.2°, 18.5±0.2°, and 21.6±0.2° of the crystal disclosed in CN 102336693. It indicates that the high melting point Carboprost Tromethamine crystal is a novel crystalline form of Carboprost Tromethamine.

In one embodiment of the present invention, the Carboprost Tromethamine crystal has an XRPD pattern exhibiting characteristic peaks at the following 20 reflection angles: 6.9±0.2°, 10.3±0.2°, 18.8±0.2°, and 21.9±0.2°. In a preferred embodiment, the XRPD pattern further comprises characteristic peaks at the following 20 reflection angles: 9.1±0.2°, 9.5±0.2°, 11.0±0.2°, and 20.5±0.2°. More preferably, the XRPD pattern of the Carboprost Tromethamine crystal is consistent with FIG. 1. The particular data of the Carboprost Tromethamine crystal is shown in Table 1.

TABLE 1

| 2θ angle (°) | d value (Å) | relative intensity (%) |
|---|---|---|
| 6.92 | 12.76 | 100.00 |
| 9.08 | 9.73 | 5.20 |
| 9.49 | 9.31 | 4.77 |
| 9.83 | 8.99 | 3.23 |
| 10.26 | 8.61 | 25.37 |
| 11.02 | 8.02 | 2.76 |
| 12.52 | 7.06 | 1.34 |
| 13.16 | 6.72 | 2.55 |
| 13.61 | 6.50 | 2.37 |
| 13.97 | 6.33 | 1.59 |
| 14.48 | 6.11 | 2.23 |
| 16.10 | 5.50 | 3.91 |
| 16.84 | 5.26 | 4.47 |
| 16.97 | 5.22 | 5.06 |

TABLE 1-continued

| 2θ angle (°) | d value (Å) | relative intensity (%) |
|---|---|---|
| 17.41 | 5.09 | 1.93 |
| 17.72 | 5.00 | 4.65 |
| 17.99 | 4.93 | 7.48 |
| 18.43 | 4.81 | 8.92 |
| 18.81 | 4.71 | 31.86 |
| 19.58 | 4.53 | 20.95 |
| 19.77 | 4.49 | 28.20 |
| 20.17 | 4.40 | 24.25 |
| 20.35 | 4.36 | 17.83 |
| 20.54 | 4.32 | 12.33 |
| 21.07 | 4.21 | 8.03 |
| 21.42 | 4.15 | 6.27 |
| 21.86 | 4.06 | 16.88 |
| 22.77 | 3.90 | 2.06 |
| 23.57 | 3.77 | 2.88 |
| 23.98 | 3.71 | 2.97 |
| 24.25 | 3.67 | 3.18 |

In one embodiment, the present invention provides a crystalline form of Carboprost Tromethamine having an XRPD pattern substantially as shown in FIG. 1.

Figure 3:
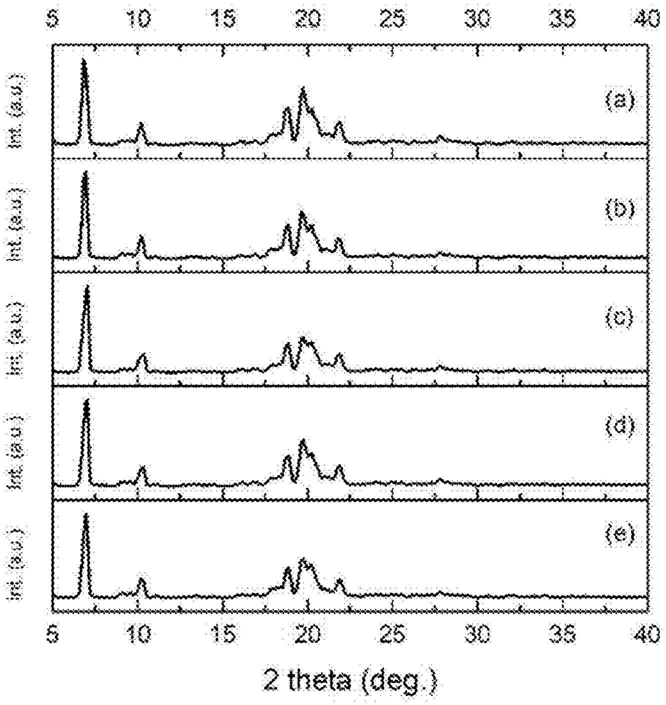
FIG. 3 shows the X-ray powder diffraction (XRPD) patterns of the Carboprost Tromethamine crystals for five different batches according to the present invention.

In one embodiment, the present invention provides the XRPD patterns of the Carboprost Tromethamine crystals for five different batches (a) to (e), as shown in FIG. 3. The particular data of the four major separated characteristic peaks are clearly marked and shown in Table 2. The average positions of characteristic peaks are located at about 6.9°, 10.3°, 18.8°, and 21.9°, respectively.

TABLE 2

| Sample | 2θ angle (°) | | | |
|---|---|---|---|---|
| (a) | 6.87 | 10.21 | 18.80 | 21.88 |
| (b) | 6.92 | 10.22 | 18.80 | 21.87 |
| (c) | 7.02 | 10.32 | 18.82 | 21.87 |
| (d) | 7.00 | 10.29 | 18.81 | 21.88 |
| (e) | 6.91 | 10.25 | 18.82 | 21.90 |
| Average | 6.94 | 10.26 | 18.81 | 21.88 |

The XRPD characteristic peak positions of the Carboprost Tromethamine crystal of the present invention locate at higher 2-theta (2θ) angle (6.9±0.2°, 10.3±0.2°, 18.8±0.2°, and 21.9±0.2°), comparing with 6.6±0.2°, 9.9±0.2°, 18.5±0.2°, and 21.6±0.2° disclosed by CN102336693. The characteristic peak at 6.621° of Carboprost Tromethamine disclosed by CN 102336693 represents a d-spacing of 13.3397 Å. On the other hand, the characteristic peak at 6.92° of Carboprost Tromethamine of the present invention represents a d-spacing of 12.76 Å. The more than 0.5 Å d-spacing difference is a very clear evidence indicating that the molecule packing are different in crystal lattice structure. This result shows that the Carboprost Tromethamine crystal is a novel crystalline form with a more stable and denser ordering packing structure comparing to the previous arts.

Figure 2:
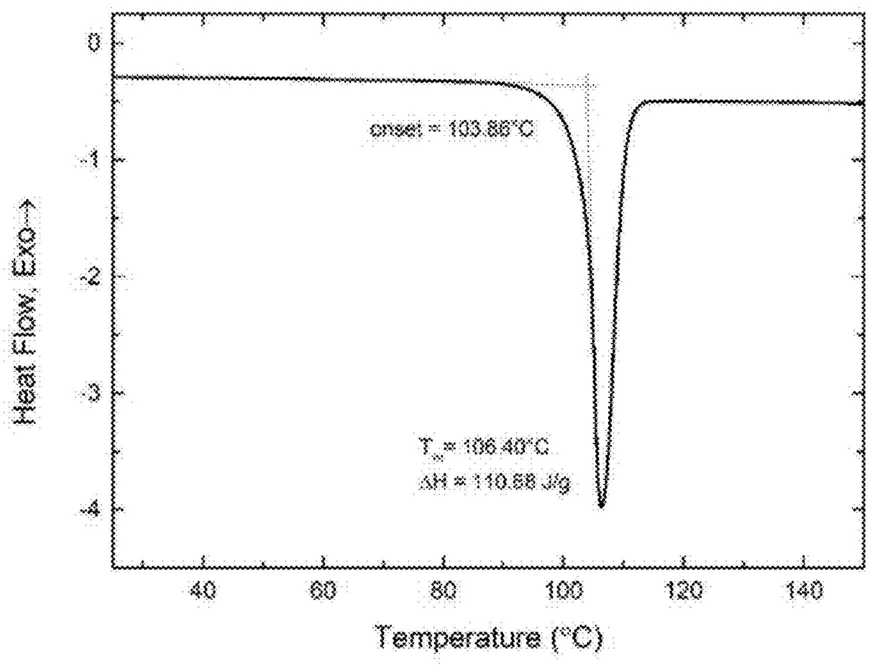
FIG. 2 shows the differential scanning calorimetry (DSC) thermogram pattern of the Carboprost Tromethamine crystal of the present invention.

In one embodiment, the present invention provides a Carboprost Tromethamine crystal having a DSC thermogram pattern comprising an endothermic peak with a peak onset temperature of approximately 103.9° C. and a peak maximum of approximately 106.4±1.0° C. In a preferred embodiment, the present invention provides a crystalline form of Carboprost Tromethamine having a DSC thermogram pattern substantially as shown in FIG. 2.

Figure 4:
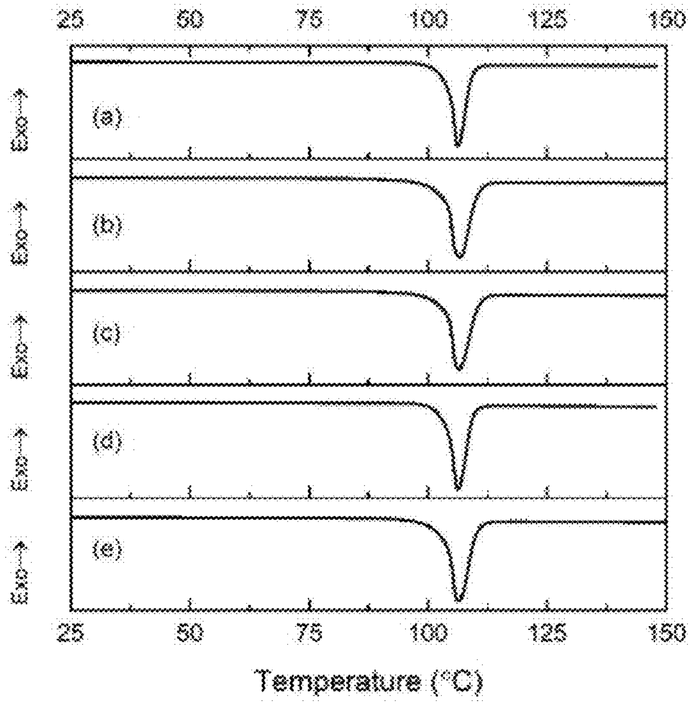
FIG. 4 shows the differential scanning calorimetry (DSC) thermogram patterns of the Carboprost Tromethamine crystals for five different batches according to the present invention.

In one embodiment, the present invention provides the DSC thermogram patterns of the Carboprost Tromethamine crystals for five different batches (a) to (e), as shown in FIG. 4. The particular data of the peak maximum for single endothermic peak is clearly marked and shown in Table 3. The average peak maximum of these endothermic peaks is about 106.4° C.

TABLE 3

| Sample | Peak Maximum (° C.) |
|---|---|
| (a) | 106.27 |
| (b) | 106.63 |
| (c) | 106.44 |
| (d) | 106.34 |
| (e) | 106.40 |
| Average | 106.42 |

The DSC peak maximum temperature of about 106.4° C. for the Carboprost Tromethamine crystal of the present invention is far beyond the disclosed melting point of Carboprost Tromethamine of 95 to 105° C. (as originally provided by Pfizer) and the peak maximum temperature of 103.97° C. disclosed in CN 102336693, indicating that the Carboprost Tromethamine crystal of the present invention is a novel crystal with higher thermal stability comparing to the previous arts. It is well-known for person skilled in the art that a crystal comprising the highest melting point is the most stable crystalline form in thermodynamics; hence, the novel Carboprost Tromethamine crystal of the present invention is the most stable one compared to the previous arts.

The United States Pharmacopeia recommends that Carboprost Tromethamine should be stored in a freezer (−20° C.). In contrast, the present invention proves that the high melting point crystalline form of Carboprost Trometiamine is very stable even being treated at 20° C. for 6 months, 5° C. for 18 months, and 80° C. for 3 days. Hence, the stability of the Carboprost Tromethamine crystal of present invention has been significantly improved.

All of the compounds and/or processes disclosed and claimed herein can be made and executed without undue experimentation in light of the present disclosure. While the compounds and process of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutions and modifications apparent to those skilled in the art are deemed to be within the spirit, scope and concept of the invention as defined by the appended claims.

EXAMPLES

X-ray Powder Diffraction (XRPD) Analysis: The XRPD patterns were collected on a Bruker D2 PHASER diffractometer with fixed divergence slits and 1D LYNXEYE detector. The samples (ca. 100 mg) were flatly placed on a sample holder. The prepared samples were analyzed over a 2θ range from 5° to 40° with step size of 0.02 degrees and step time of 1 second using $CuK_{\alpha}$ radiation at a power of 10 mA and 30 kV. The $CuK_{\beta}$ radiation was removed by a divergent beam nickel filter.

Differential Scanning Calorimetry (DSC) Analysis: The DSC thermogram patterns were collected on a TA DISCOVERY DSC25 instrument. The samples were weighed into an aluminum pan with a crimping closed aluminum lid. The prepared samples were analyzed from 25° C. to 150° C. at scan rate of 10° C./min under a flow of nitrogen (ca. 50 mil/min). The melting temperature and heat of fusion were calibrated by indium (In) before measurement. The melting point of all samples was determined by the peak maximum of the endothermic peak during DSC measurement in this invention.

Example 1

(8aR,9R,10R,11aS,Z)-10-((tert-butyldimethylsilyl)oxy)-9-((S,E)-3-((tert-butyldimuethyl-silyl)oxy)oct-1-en-1-yl)-4,5,8,8a,9,10,11,11a-octahydrocyclopenta[b]oxecin-2(3H)-one

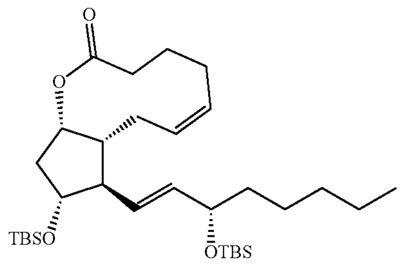 [SMILES: CCCCC[C@@H](/C=C/[C@@H]1[C@H]2C/C=C\CCCC(=O)O[C@H]2C[C@H]1O[Si](C)(C)C(C)(C)C)O[Si](C)(C)C(C)(C)C]

The 1.4 kg of 7-((1R,2R,3R,5S)-3-((tert-butyldimethylsilyl)oxy)-2-((S,E)-3-((tert-butyldimethylsilyl)oxy)oct-1-en-1-yl)-5-hydroxycyclopentyl)hept-5(Z)-enoic acid, which includes about 6.5% of 5,6-trans isomer determined by detecting it's deprotected product in HPLC analysis, and 475 g of pyridine were dissolved in 6.5 L of dichloromethane at ambient temperature under nitrogen. Then, 843 g of benzoyl chloride was added into the mixture and stirred for one hour. The reaction mixture was checked by TLC to confirm completion of the reaction. The mixture was quenched with 6 L of saturated sodium bicarbonate aqueous solution and stirred for 10 minutes. The solution was stand to separate into two phases, and an organic layer was collected. The organic layer was further evaporated off. The concentrated residue was diluted with 6 L of Toluene, and washed with 0.1N hydrochloric acid aqueous solution and brine, respectively. The organic layer was collected and evaporated off to obtain crude silyl-protected 1,9-lactone compound. The crude compound was further purified by chromatography on silica gel using a mixture of hexane and ethyl acetate as a gradient eluent. Yield of the obtained silyl-protected 1,9-lactone was 1.0 kg (74%).

The 0.1 g of product was further processed with hydrolysis reaction and deprotection reaction to obtain the crude product. HPLC analysis showed that no 5,6-trans isomer was detectable for the crude compound.

$^1$H-NMR ($CDCl_3$): δ 5.156~5.595 (m, 5H), 4.067 (q, 1H), 3.809 (q, 1H), 1.247~2.532 (m, 20H), 0.852~0.898 (m, 21H), −0.005~0.034 (m, 12H); $^{13}$C-NMR ($CDCl_3$): δ 173.620, 136.520, 131.169, 129.135, 127.890, 72.809, 72.088, 55.345, 44.567, 41.599, 38.669, 36.134, 31.831, 26.730, 26.571, 25.895, 25.835, 25.349, 25.136, 22.624, 18.222, 18.063, 14.047, −4.252, −4.556, −4.579, 4.768; MS (m/z, EI): Calculated for $C_{32}H_{60}O_4Si_2Na$ ($M^+$): 587.4 and 587.5 found.

Example 2

(8aR,9R,10R,11aS,Z)-9-((S,E)-3-((tert-butyldimethylsilyl)oxy)oct-1-en-1-yl)-10-((tetra-hydro-2H-pyran-2-yl)oxy)-4,5,8,8a,9,10,11,11a-octahydrocyclopenta[b]oxecin-2(3H)-one

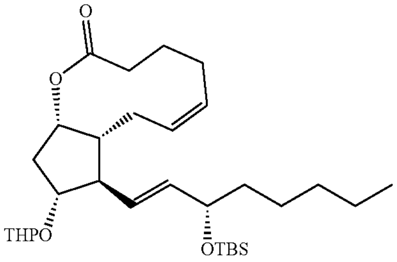

The 2.0 g of 7-((1R,2R,3R,5S)-2-((S,E)-3-((tert-butyldimethylsilyl)oxy)oct-1-en-1-yl)-5-hydroxy-3-((tetrahydro-2H-pyran-2-yl)oxy)cyclopentyl)hept-5(Z)-enoic acid, which includes 1.8% of 5,6-trans isomer, determined by detecting it's deprotected compound in HPLC analysis, and 0.72 g of pyridine were dissolved in 20 ml of dichloromethane at ambient temperature under nitrogen. Then, 1.27 g of benzoyl chloride was added into the mixture and stirred for 30 minutes. The reaction mixture was checked by TLC to confirm completion of the reaction. The mixture was quenched with 15 ml of saturated sodium bicarbonate aqueous solution and stirred for 10 minutes. The solution was stand to separate into two phases, and an organic layer was collected. The organic layer was evaporated off, and the crude ether-protected 1,9-lactone compound was obtained. The crude compound was purified by chromatography on silica gel using a mixture of hexane and ethyl acetate as a gradient eluent. Yield of the obtained ether-protected 1,9-lactone was 1.35 g (70%).

The 0.1 g of product was further processed with hydrolysis reaction and deprotection reaction to obtain the crude product. HPLC analysis showed that no 5,6-trans isomer was detectable for the crude compound.

$^1$H-NMR ($CDCl_3$): δ5.172~5.630 (m, 5H), 4.813~4.944 (m, 1H), 3.428~4.091 (m, 4H), 1.230~2.619 (m, 26H), 0.845~0.879 (m, 12H), 0.012~0.038 (m, 6H); $^{13}$C-NMR ($CDCl_3$): δ 173.635 (173.559), 136.778 (136.619), 131.260, 129.666, (129.507), 127.640, 95.390 (94.623), 81.933 (77.910), 73.159, 62.457 (61.106), 53.971 (53.106), 44.962 (44.855), 39.618, 38.662 (38.578), 37.417, 31.816 (31.778), 30.639 (30.601), 26.730, 25.417, 25.319, 24.962, 22.601, 19.732 (19.573), 18.237 (18.222), 14.009, −4.252, −4.267, −4.806, −4.844; MS (m/z, EI): Calculated for $C_{31}H_{54}O_5SiNa$ ($M^+$): 557.4 and 557.4 found.

Example 3

(8aR,9R,10R,11aS,Z)-9-((E)-3-oxooct-1-en-1-yl)-10-((tetrahydro-2H-pyran-2-yl)oxy)-4,5,8,8a,9,10,11,11a-octahydrocyclopenta[b]oxecin-2(3H)-one

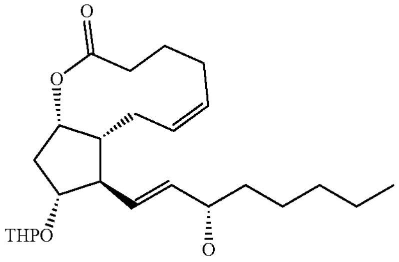

The 1.5 g of 7-((1R,2R,3R,5S)-5-hydroxy-2-((E)-3-oxooct-1-en-1-yl)-3-((tetrahydro-2H-pyran-2-yl)oxy)cyclopentyl)hept-5(Z)-enoic acid and 0.68 g of pyridine were dissolved in 15 ml of dichloromethane at ambient temperature under nitrogen. Then, 1.21 g of benzoyl chloride was added into the mixture and stirred for 30 minutes. The reaction mixture was checked by TLC to confirm completion of the reaction. The mixture was quenched with 10 ml of saturated sodium bicarbonate aqueous solution and stirred for 10 minutes. The solution was stand to separate into two phases, and an organic layer was collected. The organic layer was evaporated off, and the crude 1,9-lactone compound was obtained. The crude compound was purified by chromatography on silica gel using a mixture of hexane and ethyl acetate as a gradient eluent. Yield of the obtained 1,9-lactone was 1.02 g (71%).

$^1$H-NMR ($CDCl_3$): δ 6.688 (ddd, 1H), 6.235 (dd, 1H), 5.326 (dt, 1H), 5.197 (br s, 2H), 4.592 (t, 0.5H), 4.550 (t, 0.5H), 4.060 (dd, 0.5H), 3.952 (dd, 0.5H), 3.692~3.800 (m, 1H), 3.388~3.447 (m, 1H), 1.236~2.684 ((m, 26H), 0.887 (t, 3H); $^{13}$C-NMR ($CDCl_3$): δ 200.466 (200.299), 173.499 (173.408), 146.569 (146.417), 131.951, 131.784, 126.873, 96.321 (96.612), 81.386 (78.790), 72.445 (72.111), 62.646 (61.736), 54.130 (53.546), 45.030 (44.939), 40.582 (40.309), 39.808 (38.024), 35.998, 31.451 (31.421), 30.677 (30.601), 26.715, 25.364 (25.303), 23.952, 22.442, 19.550, 18.988, 13.895; MS (m/z, EI): Calculated for $C_{25}H_{38}O_5Na$ ($M+Na^+$): 441.3 and 441.3 found.

Example 4

(8aR,9R,10R,11aS,Z)-10-hydroxy-9-((S,E)-3-hydroxyoct-1-en-1-yl)-4,5,8,8a,9,10,11,11a-octahydrocyclopenta[b]oxecin-2(3H)-one

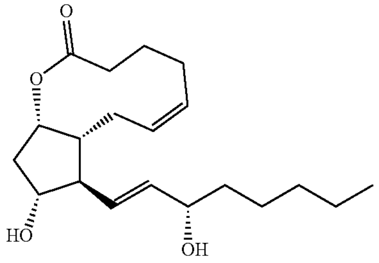 [SMILES: CCCCC[C@H](O)/C=C/[C@@H]1[C@H]2C/C=C\CCCC(=O)O[C@H]2C[C@H]1O]

The 480 g of (8aR,9R,10R,11aS,Z)-10-((tert-butyldimethylsilyl)oxy)-9-((S,E)-3-((tert-butyldimethyl-silyl)oxy) oct-1-en-1-yl)-4,5,8,8a,9,10,11,11a-octahydrocyclopenta[b] oxecin-2(3H)-one (from Example 1) was dissolved in 4.5 L of tetrahydrofuran at ambient temperature. Then, 775 g of tetrabutylammonium fluoride trihydrate was added into the solution. The homogenous solution was heated at 45° C. and stirred for 6 hours. The reaction mixture was checked by TLC to confirm completion of the reaction. The mixture was cooled down at ambient temperature and subsequently quenched with 8 L of saturated sodium bicarbonate aqueous solution. The solution was stand to separate into two phases, and an organic layer was collected. The organic layer was evaporated off to obtain crude 1,9-lactone diol compound. The crude compound was purified by chromatography on silica gel using a mixture of hexane and ethyl acetate as a gradient eluent. Then, the diol compound was further crystallized in mixed solvents of ethyl acetate and hexane. Yield of the obtained crystal of diol compound was 259 g (91%).

$^1$H-NMR ($CDCl_3$): δ 5.203~5.642 (m, 5H), 4.409 (q, 1H), 3.800 (q, 1H), 3.304 (br s, 1H), 1.281~2.608 (m, 21H), 0.868 (t, 3H); $^{13}$C-NMR ($CDCl_3$): δ 173.437, 136.785, 131.973, 131.411, 127.464, 76.065, 73.158, 71.936, 56.201, 45.074, 40.285, 37.196, 36.050, 31.655, 26.722, 26.532, 25.272, 25.158, 22.562, 13.971; MS (m/z, EI): Calculated for $C_{20}H_{30}O_4$ ($M^+$): 336.2 and 336.2 found.

Example 5

(8aR,9R,10R,11aS,Z)-10-hydroxy-9-((E)-3-oxooct-1-en-1-yl)-4,5,8,8a,9,10,11,11a-octahydrocyclopenta [b]oxecin-2(3H)-one

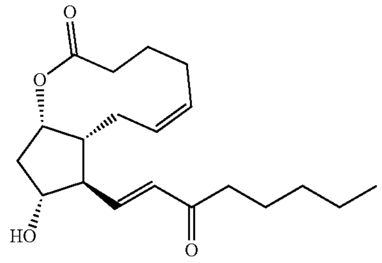 [SMILES: CCCCCC(=O)/C=C/[C@@H]1[C@H]2C/C=C\CCCC(=O)O[C@H]2C[C@H]1O]

The 300 g of (8aR,9R,10R,11aS,Z)-10-hydroxy-9-((S,E)-3-hydroxyoct-1-en-1-yl)-4,5,8,8a,9,10,11,11a-octahydrocyclo-penta[b]oxecin-2(3H)-one (from Example 4) was dissolved in 3 L of tetrahydrofuran at ambient temperature, and 2,3-dichloro-5,6-di-cyano-1,4-benzo-quinone was added. The reaction mixture was heated at 55° C. and stirred for 2 hours. After completion of reaction, the mixture was cooled down at ambient temperature and evaporated off. Then, the dark-brown residue was diluted with dichloromethane, and yellow solid was precipitated. The mixture was filtered off, and the filtrate was further concentrated to obtain a crude ketone compound. The crude compound was purified by chromatography on silica gel using a mixture of hexane and ethyl acetate as a gradient eluent. Yield of the obtained 15-keto 1,9-lactone was 276 g (93%).

$^1$H-NMR ($CDCl_3$): δ 5.183~6.686 (m, 5H), 3.991~4.062 (m, 1H), 1.251~2.642 (m, 21H), 0.887 (t, 3H); $^{13}$C-NMR ($CDCl_3$): δ 200.101, 173.316, 145.536, 132.064, 131.737, 126.865, 76.383, 72.406, 56.239, 45.591, 40.983, 40.839, 36.027, 31.435, 26.729, 25.302, 23.754, 22.433, 13.895; MS (m/z, EI): Calculated for $C_{20}H_{30}O_4$($M^+$): 334.2144 and 334.2130 found.

Example 6

(8aR,9R,10R,11aS,Z)-10-hydroxy-9-((S,E)-3-hydroxy-3-methyloct-1-en-1-yl)-4,5,8,8a,9,10,11,11a-octahydrocyclopenta[b]oxecin-2(3H)-one

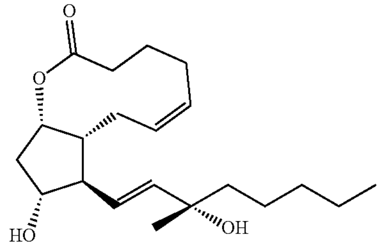 [SMILES: CCCCC[C@](C)(O)/C=C/[C@@H]1[C@H]2C/C=C\CCCC(=O)O[C@H]2C[C@H]1O]

Method A:

The 275 g of (8aR,9R,10R,11aS,Z)-10-hydroxy-9-((E)-3-oxooct-1-en-1-yl)-4,5,8,8a,9,10,11,11a-octahydrocyclopenta[b]oxecin-2(3H)-one (from Example 5) was dissolved in 4.5 L of tetrahydrofuran at ambient temperature under nitrogen and cooled down at −70° C. The 1.0 L of Methyllithium (2M in ether) was slowly added to the reaction mixture at −70° C., and the reaction was checked by TLC. After completion of reaction, the mixture was quenched with saturated ammonium chloride aqueous solution and stirred for 10 minutes. Then, 1 L of ethyl acetate was added to the reaction mixture and allowed to warm up at ambient temperature. The mixture was stand to separate into two phases, and an organic layer was collected and dried over anhydrous Sodium sulfate. Subsequently, the solid was filtered off and the filtrate was evaporated off. The crude 15-methyl mixture compound was obtained and tested by HPLC. The ratio of 15-R/15-S of the crude compound is about 25/75. The crude compound was further purified by chromatography on silica gel using a mixture of dichloromethane and acetone as a gradient eluent. Yield of the obtained pure 15-methyl compound was 163 g (57%).

Method B:

The 2 g of (8aR,9R,10R,11aS,Z)-10-hydroxy-9-((E)-3-oxooct-1-en-1-yl)-4,5,8,8a,9,10,11,11a-octahydrocyclopenta[b]oxecin-2(3H)-one (from Example 5) was dissolved in 20 ml of tetrahydrofuran at ambient temperature under nitrogen and cooled down at −70° C. Then, 21 ml of methylmagnesium bromide (1M in THF) was slowly added to the reaction mixture at −70° C. and warmed up at 0° C. The mixture was checked by TLC to confirm completion of reaction. Sampling the reaction mixture to check the ratio of 15-R/15-S of the product is about 35/65.

$^1$H-NMR ($CDCl_3$): δ 5.203~5.713 (m, 5H), 3.787 (q, 1H), 1.167~2.535 (m, 25H), 0.859 (t, 3H); $^{13}$C-NMR ($CDCl_3$): δ 173.399, 140.709, 131.336, 127.556, 127.526, 76.331, 72.840, 72.187, 56.233, 45.281, 42.875, 40.317, 36.029, 32.173, 27.520, 26.693, 26.579, 25.274, 23.801, 22.541, 13, 950; MS (m/z, EI): Calculated for $C_{21}H_{32}O_3$($M^+$-$H_2O$): 332.2351 and 332.2349 found.

Example 7

(8aR,9R,10R,11aS,Z)-10-((tert-butyldimethylsilyl)oxy)-9-((S,E)-3-hydroxy-3-methyloct-1-en-1-yl)-4,5,8,8a,9,10,11,11a-octahydrocyclopenta[b]oxecin-2(3H)-one

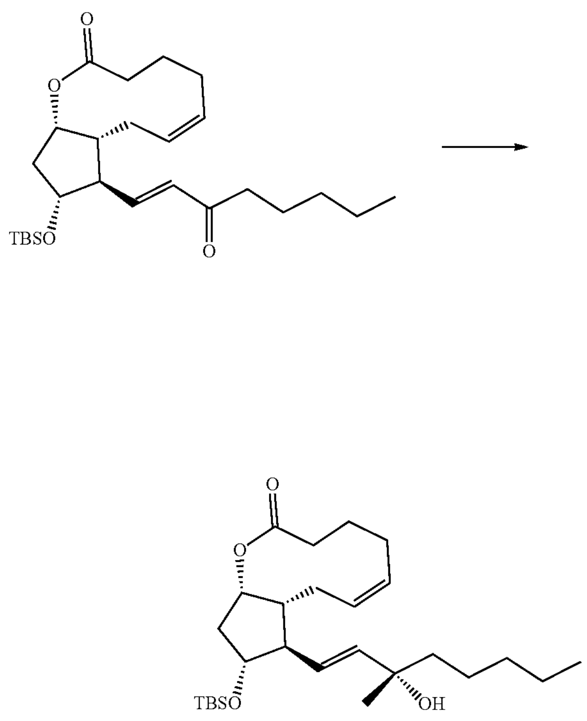

The 2.0 g of (8aR,9R,10R,11aS,Z)-10-((tert-butyldimethylsilyl)oxy)-9-((E)-3-oxooct-1-en-1-yl)-4,5,8,8a,9,10,11,11a-octahydrocyclopenta[b]oxecin-2(3H)-one in 20 ml of tetrahydrofuran at ambient temperature and cooled down at −70° C. The 3.5 ml of methyllithium (2M in ether) was slowly added to the reaction mixture at −70° C., and the reaction was checked by TLC. After completion of reaction, the mixture was quenched with saturated ammonium chloride aqueous solution and stirred for 10 minutes. Then, 1 ml of ethyl acetate was added to the reaction mixture and allowed to warmed up at ambient temperature. The mixture was phase separated, and an organic layer was dried over anhydrous sodium sulfate. Subsequently, the solid was filtered off, and the filtrate was evaporated off to obtain a crude 15-methyl mixture compound. The crude compound was purified by chromatography on silica gel using a mixture of dichloromethane and acetone as a gradient eluent. Yield of the obtained pure 15-methyl compound was 1.05 g (51%).

$^1$H-NMR ($CDCl_3$): δ 5.168~5.689 (m, 5H), 3.807 (q, 1H), 1.258~2.551 (m, 24H), 0.857~0.944 (m, 12H), 0.011 (s, 6H); $^{13}$C-NMR ($CDCl_3$): δ 173.582, 140.368, 131.275, 127.746, 127.678, 76.954, 72.938, 72.005, 55.610, 44.483, 42.844, 41.569, 36.127, 32.279, 28.081, 26.738, 26.487, 25.789, 23.839, 22.579, 18.070, 14.040, −3.592, −4.518, −4.624.

MS (m/z, EI): Calculated for $C_{27}H_{48}O_4SiNa$ (M+Na$^+$): 487.3 and 487.3 found.

Example 8

(Z)-7-((1R,2R,3R,5S)-3,5-dihydroxy-2-((S,E)-3-hydroxy-3-methyloct-1-en-1-yl)cyclo-pentyl)hept-5-enoic Acid, Carboprost

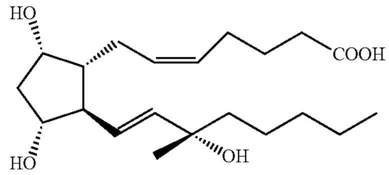 [SMILES: CCCCC[C@](C)(O)/C=C/[C@@H]1[C@@H](C/C=C\CCCC(=O)O)[C@@H](O)C[C@H]1O]

The 143 g of (8aR,9R,10R,11aS,Z)-10-hydroxy-9-((S,E)-3-hydroxy-3-methyloct-1-en-1-yl)-4,5,8,8a,9,10,11,11a-octahydrocyclopenta[b]oxecin-2(3H)-one (from Example 6) was dissolved in 750 ml of methanol, and 1.5 L of 1N lithium hydroxide aqueous solution was added. The reaction mixture was heated at 60° C. for 2 hours. After completion of reaction, the mixture was cooled down at room temperature, and pH value of the solution was adjusted to about 8.5. The mixture was concentrated to remove methanol and the residue was further purified by acid-base extraction. Yield of the obtained Carboprost was 129 g.

$^1$H-NMR ($CDCl_3$): δ 5.278~5.610 (m, 7H), 4.112~4.133 (m, 1H), 3.866~3.911 (m, 1H), 1.252~2.298 (m, 23H), 0.843 (t, 3H);

$^{13}$C-NMR ($CDCl_3$): δ 177.316, 138.903, 129.431, 129.226, 128.839, 77.599, 73.333, 72.339, 55.292, 50.427, 42.731, 42.488, 33.031, 32.257, 26.966, 26.245, 25.099, 24.507, 23.809, 22.610, 14.063;

MS (m/z, EI): Calculated for $C_{21}H_{34}O_4$ (M$^+$-$H_2O$): 350.2 and 350.3 found.

Example 9

Carboprost Tromethamine Salt Formation 2-amino-2-(hydroxymethyl)propane-1,3-diol; (Z)-7-((1R,2R,3R,5S)-3,5-dihydroxy-2-((S,E)-3-hydroxy-3-methyloct-1-en-1-yl)cyclopentyl)hept-5-enoate, Carboprost Tromethamine

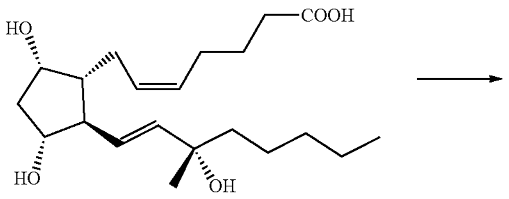

Carboprost

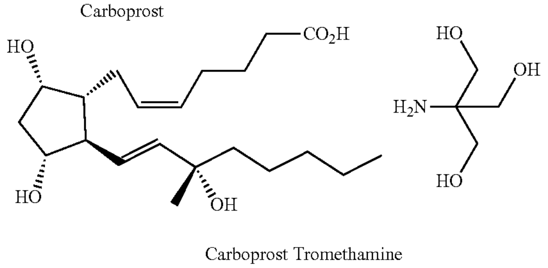

Carboprost Tromethamine

Figure 5:
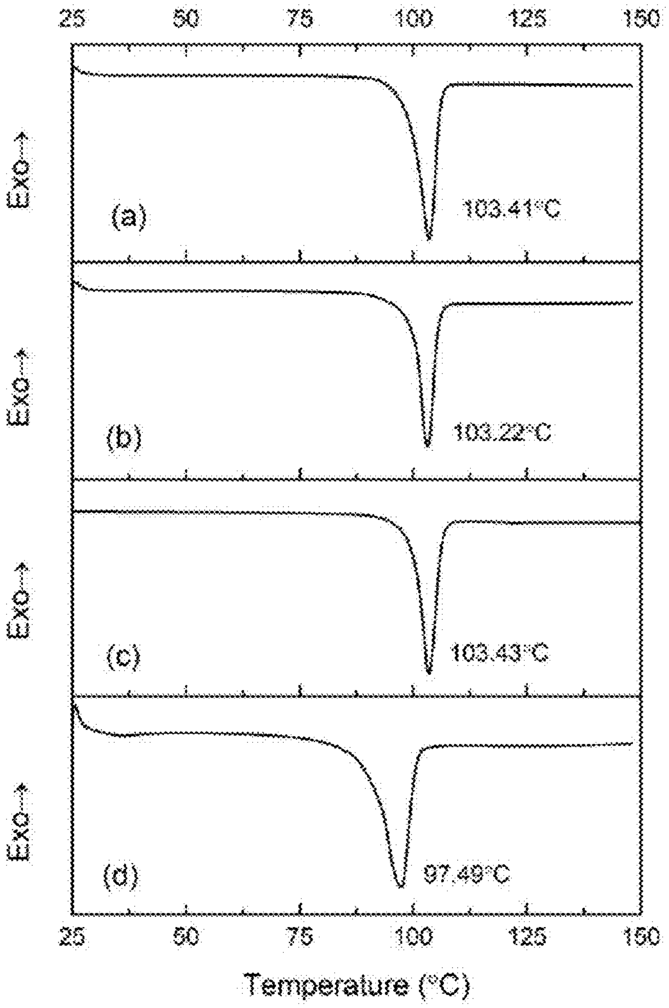
FIG. 5 shows the differential scanning calorimetry (DSC) thermogram patterns of the Carboprost Tromethamine crystals prepared from Example 9 of present invention.

Method A:

The 114 g of Carboprost was dissolved in 1.2 L of acetonitrile at 60° C., and the solution was heated to 65° C. The 37.4 g of tromethamine in 120 ml water was slowly added into the solution. The reaction mixture was further heated to 85° C. for reflux for 10 minutes. The homogenous solution was allowed to cool down to 60° C., and the white solid was slowly started to precipitate. The mixture was further cooled down to room temperature and stirred over 16 hours. The reaction mixture was filtered to obtain white crystalline form of Carboprost Tromethamine (118 g). The melting point of the crystal was measured by DSC as 103.41° C., as shown in FIG. 5(*a*).

$^{1}$H-NMR ($D_2O$): δ 5.336~5.594 (m, 4H), 4.109 (br s, 1H), 3.819 (br s, 1H), 3.632 (s, 6H), 1.193~2.427 (m, 23H), 0.764 (t, 3H);

$^{13}$C-NMR ($CDCl_3$): δ 183.433, 138.523, 130.584, 129.203, 128.854, 75.928, 73.576, 71.109, 71.109, 61.257, 59.451, 54.327, 41.971, 41.902, 37.136, 31.565, 26.601, 25.850, 25.743, 24.779, 23.277, 21.888, 13.288:

MS (m/z, ESI): Calculated for $C_{25}H_{48}NO_8$ ($MH^+$): 490.3374 and 490.3384 found.

Method B:

The Carboprost Tromethamine crystal was prepared from an acetone/aqueous solution by following the method disclosed in Example 3 of CN 102336693. The melting point of the crystal was measured by the inventor as 103.22° C., as shown in FIG. 5(*b*).

Method C:

The Carboprost Tromethamine crystal was prepared from an ether/aqueous solution by following the method disclosed in Example 7 of CN 102336693. The melting point of the crystal was measured by the inventor as 103.43° C., as shown in FIG. 5(*c*).

Method D:

The Carboprost Tromethamine crystal was prepared from an isopropanol/acetone solution by following the method disclosed in Example 1g of WO 2017/093770. The melting point of the crystal was measured by the inventor as 97.49° C., as shown in FIG. 5(*d*).

Example 10

Recrystallization of Carboprost Tromethamine

Figure 6:
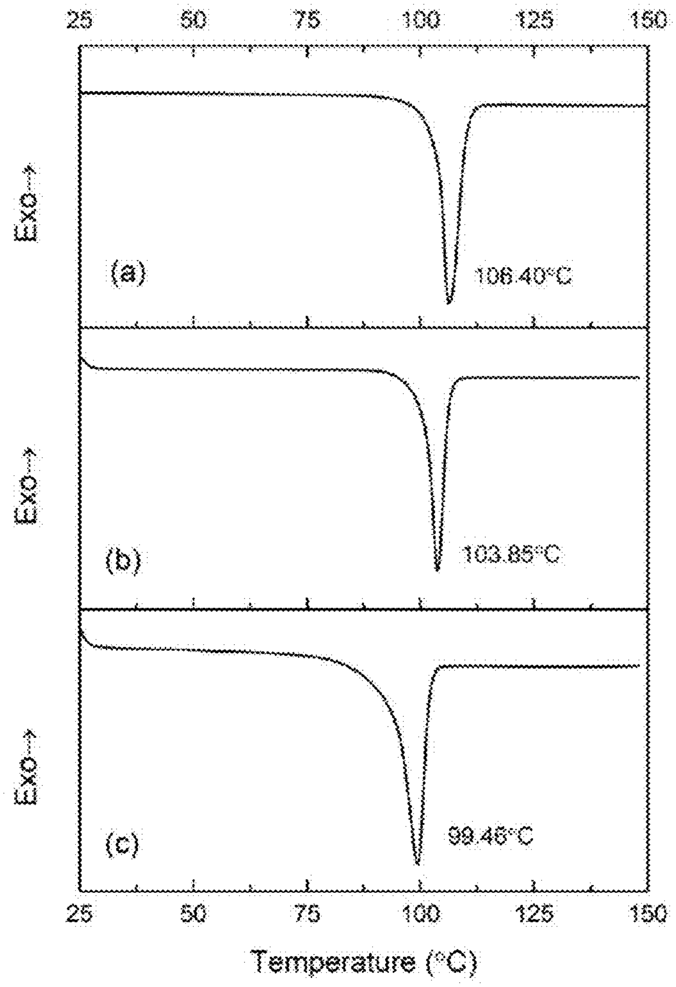
FIG. 6 shows the differential scanning calorimetry (DSC) thermogram patterns of the Carboprost Tromethamine crystals prepared from Example 10 of present invention.

Method A:

10.0 g Carboprost Tromethamine was dissolved in 1 L acetonitrile containing water of 0.02% at 85° C. to give a homogeneous solution and then cooled down the homogeneous solution to 60° C., and the white solid was slowly started to precipitate. The mixture was further cooled down to room temperature. The resulting precipitate crystal was filtered and dried. After recrystallization, yield of the obtained high purity Carboprost Tromethamine crystal was 9.0 g. The melting point of the crystal was measured by DSC as 106.40° C., as shown in FIG. 6(*a*). Upon HPLC analysis, 15(R)-epimer was in an amount of 0.05%, and 5,6-trans isomer was not detected.

Method B:

The Carboprost Tromethamine crystal was prepared from an acetone/aqueous solution by following the method disclosed in Example 2, 4, 6, or 8 of CN 102336693. The melting point of the crystal was measured by the inventor as 103.85° C., as shown in FIG. 6(*b*).

Method C:

The Carboprost Tromethamine crystal was prepared from an isopropanol/acetone solution by following the method disclosed in Example 1h of WO2017093770. The melting point of the crystal was measured by the inventor as 99.46° C., as shown in FIG. 6(*c*).

Example 11

Purification of Low Purity Carboprost Tromethamine 3 g of commercially available Carboprost Tromethamine, which includes 2.5% of 5,6-trans isomer and 1.5% 15(R)-epimer, was dissolved in acidic water with pH of 3 and extracted with ethyl acetate to obtain 2 g of Carboprost. A solution of Carboprost in 8 ml of anhydrous, oxygen-free xylene was treated with 1.73 g of 2,2'-dipyridyl disulfide and 2.06 g of triphenylphosphine. After stirring for 18 hours at 25° C., the mixture was diluted with 500 ml of xylene and heated at reflux for 4 hours. The reaction mixture was further evaporated to remove the solvent, and the residue was partitioned between a cold sodium bicarbonate aqueous solution and ethyl acetate. The organic layer was collected and washed with brine, and dried with anhydrous sodium sulfate. The mixture was filtered and concentrated to obtain crude 1,9-lactone compound. The crude compound was purified by chromatography on silica gel using a mixture of dichloromethane and acetone as a gradient eluent. Yield of the obtained 15-methyl 1,9-lactone was 1.67 g.

The 1,9-lactone product was further processed by a hydrolysis reaction to obtain Carboprost which includes 2.5% of 15(R)-epimer but no detectable 5,6-trans isomer in HPLC analysis. Carboprost Tromethamine was formed from the Carboprost and tromethamine according to the process of Example 9, and crystallized and recrystallized according to the process of Example 10 (Method A) and Example 11 to obtain high purity Carboprost Tromethamine. Upon HPLC analysis, 15(R)-epimer was in an amount of 0.15%, and 5,6-trans isomer was not detected.

Example 12

Stability of Caboprost Tromethamine Crystal

The stability data shown in Tables 4 and 5 shows that the high melting point Carboprost Tromethamine crystal is stable even being treated at 20° C. for 6 months, PC for 18 months, and 80° C. for 3 days. The high melting point Carboprost Tromethamine Crystal is very stable at room temperature, even at higher temperature, so that the formation of degradation impurities can be effectively avoided.

TABLE 4

| Specimen | Carboprost Tromethamine crystal | Carboprost Tromethamine crystal | Carboprost Tromethamine crystal |
|---|---|---|---|
| Conditions | Control | 25° C./60% RH 1 month | 25° C./60% RH 6 months |
| Purity | 99.75% | 99.71% | 99.75% |
| 15(R)-epimer | 0.25% | 0.27% | 0.25% |
| 5,6-trans isomer | ND | ND | ND |
| Total Impurities | 0.25% | 0.29% | 0.25% |
| Conditions | 5° C. 1 month | 5° C. 12 months | 5° C. 18 months |
| Purity | 99.72% | 99.75% | 99.75% |
| 15-epi | 0.28% | 0.25% | 0.25% |
| 5,6-trans isomer | ND | ND | ND |
| Total Impurities | 0.28% | 0.25% | 0.25% |

TABLE 5

| Specimen | Carboprost Tromethamine crystal | Carboprost Tromethamine crystal | Carboprost Tromethamine crystal |
|---|---|---|---|
| Conditions | Control | 80° C. 1 days | 80° C. 3 days |
| Purity | 99.79% | 99.79% | 99.78% |
| 15-epi | 0.21% | 0.20% | 0.21% |
| 5,6-trans isomer | ND | ND | ND |
| Total Impurities | 0.21% | 0.21% | 0.22% |

On the other hand, the hygroscopicity of the high melting point Carboprost Tromethamine crystal prepared from Example 10 (Method A) and the low melting point Carboprost Tromethamine crystal prepared from Example 10 (Method B) was measured. The samples were placed in glass vial with 99% RH at 25° C. for 3 hours, and the water content of the samples were measured by Karl Fischer titration, as shown in Table 6. The high melting point Carboprost Tromethamine crystal shows a relatively low rate of water absorption compared to the low melting point one, indicating that the high melting point Carboprost Tromethamine crystal is more stable and can be stored for a longer time under high humidity condition, so the high melting point Carboprost Tromethamine crystal is more conducive to product handling, storage and shipping.

TABLE 6

| Specimen | Example 10 (Method A) high melting point | Example 10 (Method B) low melting point |
|---|---|---|
| Conditions | Water Content (%) | |
| Original | 0.36571% | 0.33029% |
| 25° C./99% RH/1 h | 1.50916% | 2.23611% |
| 25° C./99% RH/2 h | 3.35425% | 5.44951% |
| 25° C./99% RH/3 h | 5.88095% | 7.51338% |

What is claimed is:

1. A process for preparing Carboprost containing no more than 0.5% 15R-epimer, the process comprising the steps of:

(a) preparing a compound of Formula 3 with a 15(S) selectivity greater than 50%,

3

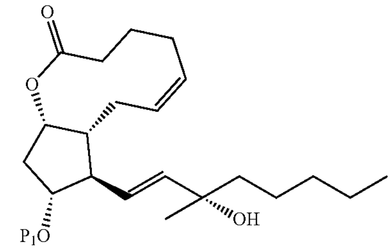

wherein $P_1$ is H or a protecting group for hydroxy groups, wherein the compound of formula 3 is prepared by methylation of a compound of Formula 2a', wherein $P_1$ is H or a protecting group for hydroxy groups, with a methylation reagent to form the compound of Formula 3, 2a'

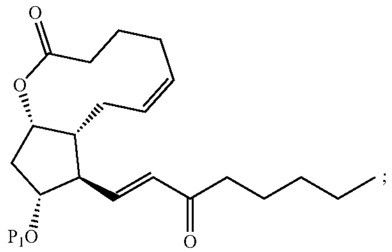

wherein the methylation reagent is MeLi;

(b) chromatographic separation of the compound of Formula 3 to remove 15(R)-epimer; and (c) hydrolysis of the compound of Formula 3, to form a compound of Formula 4:

4

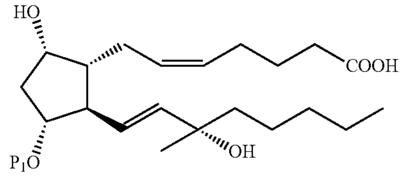

wherein $P_1$ is H or a protecting group for hydroxy groups, and optionally performing a deprotecting reaction of the compound of Formula 4, when $P_1$ is a protecting group for hydroxy groups, to form a compound of Formula 4, wherein $P_1$ is H.

2. The process according to claim 1, wherein the compound of formula 3 has a 15(S)-selectivity of about 75% or more.

* * * * *